US012799158B2

(12) United States Patent
Udugamasooriya et al.

(10) Patent No.: US 12,799,158 B2
(45) Date of Patent: Nov. 17, 2026

(54) PEPTOID COMPOUNDS THAT BIND TO CELL RECEPTOR ACE2 AND PREVENT VIRUS ENTRY INTO CELLS

(71) Applicant: UNIVERSITY OF HOUSTON SYSTEM, Houston, TX (US)

(72) Inventors: Damith Gomika Udugamasooriya, Houston, TX (US); Bin Guo, Houston, TX (US); Satya Prakash Shukla, Houston, TX (US); Kwang Bog Cho, Houston, TX (US)

(73) Assignee: University of Houston System, Houston, TX (US)

( * ) Notice: Subject to any disclaimer, the term of this patent is extended or adjusted under 35 U.S.C. 154(b) by 827 days.

(21) Appl. No.: 18/015,927

(22) PCT Filed: Apr. 7, 2021

(86) PCT No.: PCT/US2021/026218
§ 371 (c)(1),
(2) Date: Jan. 12, 2023

(87) PCT Pub. No.: WO2022/015380
PCT Pub. Date: Jan. 20, 2022

(65) Prior Publication Data

US 2023/0331777 A1 Oct. 19, 2023

Related U.S. Application Data

(60) Provisional application No. 63/053,032, filed on Jul. 17, 2020.

(51) Int. Cl.
*A61P 31/14* (2006.01)
*C07K 7/02* (2006.01)
*C07K 7/06* (2006.01)
*A61K 38/00* (2006.01)

(52) U.S. Cl.
CPC ................ *C07K 7/06* (2013.01); *A61P 31/14* (2018.01); *C07K 7/02* (2013.01); *A61K 38/00* (2013.01)

(58) Field of Classification Search
CPC .......... C07K 7/06; C07K 7/02; C07K 14/001; A61P 31/14; A61K 38/00
See application file for complete search history.

(56) References Cited

U.S. PATENT DOCUMENTS

| | | | |
|---|---|---|---|
| 10,849,875 | B2 | 12/2020 | Udugamasooriya et al. |
| 2018/0369189 | A1 | 12/2018 | Udugamasooriya et al. |

FOREIGN PATENT DOCUMENTS

| | | |
|---|---|---|
| WO | WO 2008/045120 | 4/2008 |
| WO | WO 2016/138160 | 9/2016 |

OTHER PUBLICATIONS

Desai et al, Onctotarget, vol. 7, No. 21, 30678-30690, 2016 (Year: 2016).*
Smith [Science, vol. 304, Apr. 9, 2004, 237-242] (Year: 2004).*
He et al, Molecules, 2019, 24, 1855, 1-34 (Year: 2019).*
Lu et al, International Journal of Molecular Sciences, 2016, 17, 561, 1-22 (Year: 2016).*
Chen et al. Adv. Drug Deliv. Rev. 65:1357-1369, 2013 (Year: 2013).*
International Search Report and Written Opinion for PCT/US2021/026218, mailed on Jun. 30, 2021.
Desai T J et al.: "Identification of lipid-phosphatidylserine (PS) as the target of unbiasedly selected cancer specific peptide-peptoid hybrid PPS1 ", Oncotarget, Apr. 1, 2016 (Apr. 1, 2016), pp. 30678-30690, XP055348147, DOI: 10.18632/oncotarget.8929.
Lei Yuyang et al: "SARS-CoV-2 Spike Protein Impairs Endothelial Function via Downregulation of ACE 2", Circulation Research, vol. 128, No. 9, Mar. 31, 2021 (Mar. 31, 2021), pp. 1323-1326, XP055815789, US ISSN: 0009-7330, DOI: 10.1161/CIRCRESAHA.121.318902.
Liao et al., Development of an enzymatic assay for the detection of neutralizing antibodies against therapeutic angiotensin-converting enzyme 2, Journal of Immunological Methods, 389 (2013), 52-60.
Kruse et al., Therapeutic strategies in an outbreak scenario to treat the novel coronavirus originating in Wuhan, China, Jan. 31, 2020;9:72. doi: 10.12688/f1000research.22211.2. PMID: 32117569; PMCID: PMC702975.
Li, W., Moore, M., Vasilieva, N. et al. Angiotensin-converting enzyme 2 is a functional receptor for the SARS coronavirus. Nature 426, 450-454 (2003). https://doi.org/10.1038/nature02145.
Hoffmann M, Kleine-Weber H, Schroeder S, Krüger N, Herrler T, Erichsen S, Schiergens TS, Herrler G, Wu NH, Nitsche A, Müller MA, Drosten C, Pöhlmann S. SARS-CoV-2 Cell Entry Depends on ACE2 and TMPRSS2 and Is Blocked by a Clinically Proven Protease Inhibitor. Cell. Apr. 16, 2020;181(2):271-280.e8. doi: 10.1016/j.cell.2020.02.052. Epub Mar. 5, 2020. PMID: 32142651; PMCID: PMC7102627.
R.J. Simon, R.S. Kania, R.N. Zuckermann, V.D. Huebner, D.A. Jewell, S. Banville, S. Ng, L. Wang, S. Rosenberg, C.K. Marlowe, et al., Peptoids: a modular approach to drug discovery, Proceedings of the National Academy of Sciences of the United States of America, 89 (1992) 9367-9371.

(Continued)

*Primary Examiner* — Sudhakar Katakam
(74) *Attorney, Agent, or Firm* — Farhang Amini; Shackelford, Mckinley & Norton, LLP

(57) ABSTRACT

Embodiments of the present disclosure pertain to methods of blocking virus entry into cells by associating the cells with an anti-viral peptoid to result in the blocking of virus entry into the cells. Additional embodiments of the present disclosure pertain to methods of treating or preventing a viral infection in a subject by administering an anti-viral peptoid composition to the subject to result in the blocking of virus entry into the cells of the subject. Further embodiments of the present disclosure pertain to anti-viral peptoids and compositions that include the anti-viral peptoids of the present disclosure. Additional embodiments of the present disclosure pertain to the use of the anti-viral peptoids and compositions to block virus entry into cells for numerous purposes, such as treating or preventing viral infections.

16 Claims, 28 Drawing Sheets

(56) References Cited

OTHER PUBLICATIONS

S.A. Fowler, H.E. Blackwell, Structure-function relationships in peptoids: recent advances toward deciphering the structural requirements for biological function, Organic & biomolecular chemistry, 7 (2009) 1508-1524.
Y.U. Kwon, T. Kodadek, Quantitative comparison of the relative cell permeability of cyclic and linear peptides, Chemistry & biology, 14 (2007) 671-677.
N.C. Tan, P. Yu, Y.U. Kwon, T. Kodadek, High-throughput evaluation of relative cell permeability between peptoids and peptides, Bioorganic & medicinal chemistry, 16 (2008) 5853-5861.
R.N. Zuckermann, T. Kodadek, Peptoids as potential therapeutics, Curr Opin Mal Ther, 11 (2009) 299-307.
J.M. Matharage, J.D. Minna, R.A. Brekken, D.G. Udugamasooriya, Unbiased Selection of Peptide-Peptoid Hybrids Specific for Lung Cancer Compared to Normal Lung Epithelial Cells, ACS chemical biology, 1 O (2015) 2891-2899.
A.C. Raymond, B. Gao, L. Girard, J.D. Minna, D. Gomika Udugamasooriya, Unbiased peptoid combinatorial cell screen identifies plectin protein as a potential biomarker for lung cancer stem cells, Sci Rep,9 (2019) 14954.
S.P. Shukla, D.G. Udugamasooriya, A mini-library system to investigate non-essential residues of lipid-phosphatidylserine (PS) binding peptide-peptoid hybrid PPS1, Medchemcomm, 8 (2017) 2208-2215.
D.G. Udugamasooriya, T. Kodadek, On-Bead Two-Color (OBTC) Cell Screen for Direct Identification of Highly Selective Cell Surface Receptor Ligands, Current protocols in chemical biology, 4 (2012) 35-48.
Examination Report for European Patent Application No. 21722057.3, mailed on Jun. 25, 2025.
Office Action for Japanese Patent Application No. 2023-502936, mailed on Mar. 11, 2025.
Office Action for Japanese Patent Application No. 2023-502936, mailed on Jun. 24, 2025.

* cited by examiner

ACE2P1

ACE2P2

ACE2P2D1

ACE2P1T1

ACE2P2T1

PEPTOID COMPOUNDS THAT BIND TO CELL RECEPTOR ACE2 AND PREVENT VIRUS ENTRY INTO CELLS

CROSS-REFERENCE TO RELATED APPLICATIONS

This application claims priority to U.S. Provisional Patent Application No. 63/053,032, filed on Jul. 17, 2020. The entirety of the aforementioned application is incorporated herein by reference.

BACKGROUND

Viral infections have presented significant health and economic concerns. Moreover, very limited therapeutic options exist for effectively treating and preventing viral infections. Numerous embodiments of the present disclosure address the aforementioned limitations.

SUMMARY

In some embodiments, the present disclosure pertains to methods of blocking virus entry into cells. In some embodiments, such methods include associating the cells with an anti-viral peptoid to result in the blocking of virus entry into the cells. In some embodiments, the association occurs in vitro. In some embodiments, the association occurs in vivo.

In some embodiments, the present disclosure pertains to methods of treating or preventing a viral infection in a subject. In some embodiments, such methods include administering an anti-viral peptoid composition to the subject to result in the blocking of virus entry into the cells of the subject. This in turn results in the treatment and/or prevention of a viral infection in the subject.

Additional embodiments of the present disclosure pertain to anti-viral peptoids and compositions that include the anti-viral peptoids. Further embodiments of the present disclosure pertain to the use of the anti-viral peptoids and compositions to block virus entry into cells for numerous purposes, such as treating or preventing viral infections.

DESCRIPTION OF THE DRAWINGS

FIG. 3A provides a comparison of peptides to peptoids. FIG. 3B illustrates an on-bead peptoid synthesis route. One residue of a peptoid (equivalent to an amino acid of a peptide) can be introduced in two simple chemical steps that can be completed in 15×2 second microwave pulses.

FIG. 5A provides an outline of the OBTC assay. The OBTC cell screening was performed using ACE2 receptor expressing MCF-7 cells stained with red Q-dots and ACE2 receptor negative MCF-7 cells stained with green Q-dots on 50,000 peptoid library beads. One million cells of each color were taken and mixed to 1:1 ratio and were incubated for 1 hour with beads containing one-bead one-compound library at 23° C. FIGS. 5B-C illustrate the identification of two potential hit compounds that only red cells bound. FIGS. 5D-E provide the chemical structures of potential human ACE2 binding peptoids ACE2P1 and ACE2P2.

FIG. 8A provides experimental results from an in vitro pulldown assay for ACE2P1 and ACE2P2. FIG. 8B shows general structures of dimers of ACE2P1 and ACE2P2. FIG. 8C shows experimental results from a thermal shift assay after recombinant ACE2 protein was mixed with 10 μM of ACE2P1D1 or ACE2P2D1. The thermal shift assay was carried out on a QuantStudio 3 Real-Time PCR System. FIG. 8D shows changes in melting temperatures by the peptoids.

FIG. 10D shows that the trimer (ACE2P2T1) and tetramer (ACE2P2Q1) of ACE2P2 were premixed with ACE2 for 30 minutes before the mixture was applied to the GST pull-down assay to determine if these compounds can block the interaction between ACE2 and spike protein.

(FIG. 12A) or ACE2P2D1 (FIG. 12B) for 48 hours. Cell viability was measured by a WST-1 assay.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literatures and similar materials defines a term in a manner that contradicts the definition of that term in this application, this application controls.

Viral infections have presented significant health and economic concerns. Moreover, very limited therapeutic options exist for effectively treating and preventing viral infections. Additionally, vaccines have limited abilities in providing long term protection against viral infections.

For instance, viral infections caused by severe acute respiratory syndrome-related coronavirus 2 (SARS-CoV-2) have resulted in the COVID-19 pandemic, which is currently the most urgent health and economic crisis in the world. While vaccines have been developed against SARS-CoV-2, uncertainties exist as to whether or not such vaccines could provide long-term immunity against SARS-CoV-2. Therefore, the COVID-19 pandemic is expected to last for a long period of time and force populations to adjust to new norms.

Accordingly, more effective therapeutic options are needed to treat and prevent viral infections, such as viral infections caused by SARS-CoV-2. Numerous embodiments of the present disclosure address this need.

Figure 1A:
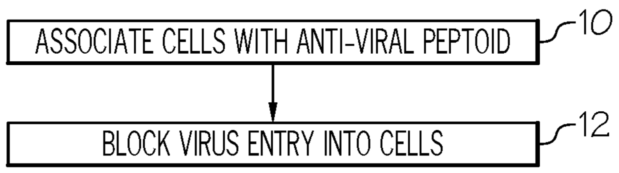
FIG. 1A illustrates a method of blocking virus entry into cells.

In some embodiments, the present disclosure pertains to methods of blocking virus entry into cells. In some embodiments illustrated in FIG. 1A, such methods include associating the cells with an anti-viral peptoid (step 10) to result in the blocking of virus entry into the cells (step 12). In some embodiments, the association occurs in vitro. In some embodiments, the association occurs in vivo.

Figure 1B:
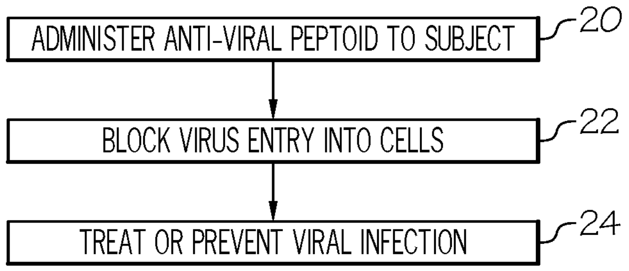
FIG. 1B illustrates a method of treating or preventing a viral infection in a subject.

In some embodiments, the present disclosure pertains to methods of treating or preventing a viral infection in a subject. In some embodiments illustrated in FIG. 1B, such methods include administering an anti-viral peptoid composition to the subject (step 20) to result in the blocking of virus entry into the cells of the subject (step 22). This in turn results in the treatment and/or prevention of a viral infection in the subject (step 24).

Additional embodiments of the present disclosure pertain to anti-viral peptoids and compositions that include the anti-viral peptoids. Further embodiments of the present disclosure pertain to the use of the anti-viral peptoids and compositions to block virus entry into cells for numerous purposes, such as treating or preventing viral infections.

As set forth in more detail herein, the present disclosure has numerous embodiments. For instance, various anti-viral peptoids and compositions can be utilized to block the entry of various viruses into various cells. Moreover, the methods of the present disclosure can be utilized to treat or prevent numerous viral infections in numerous subjects.

Anti-Viral Peptoids and Compositions

The anti-viral peptoids of the present disclosure can include numerous structures. For instance, in some embodiments, the peptoids include, without limitation one or more of the following structures:

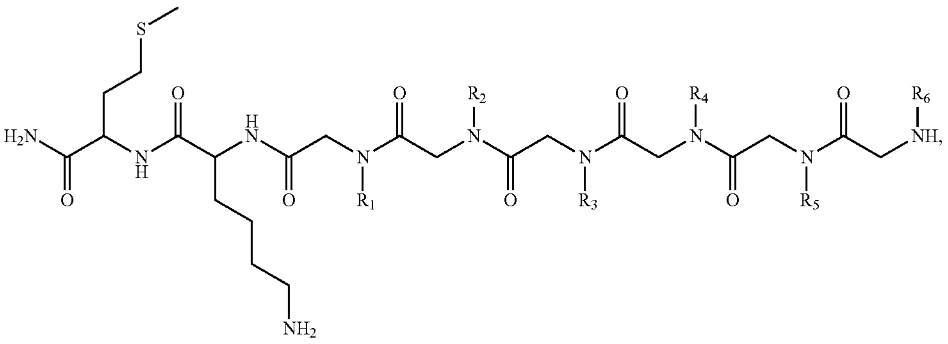
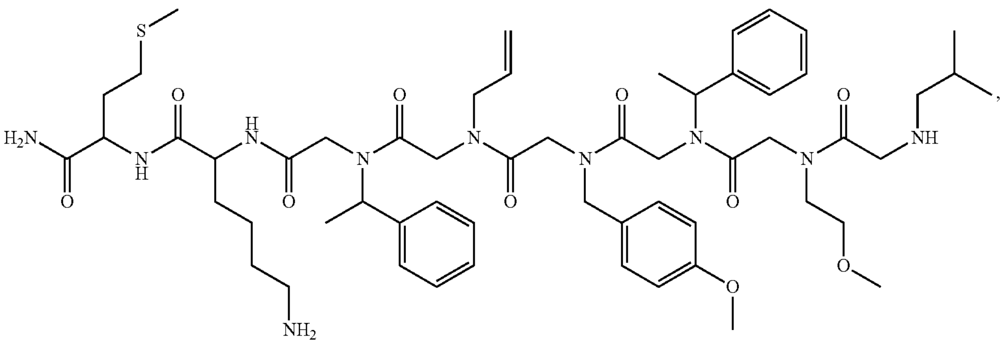
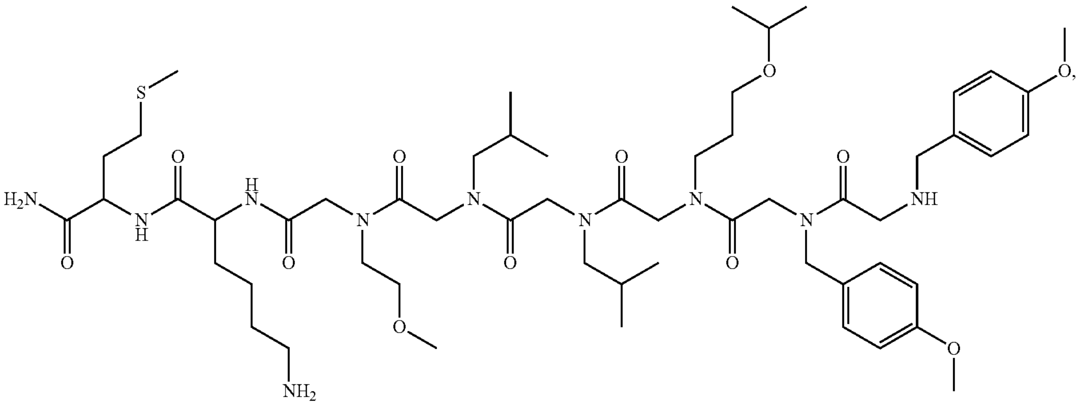
derivatives thereof, multimers thereof, or combinations thereof.

In some embodiments, the peptoid includes the following structure or a derivative thereof:

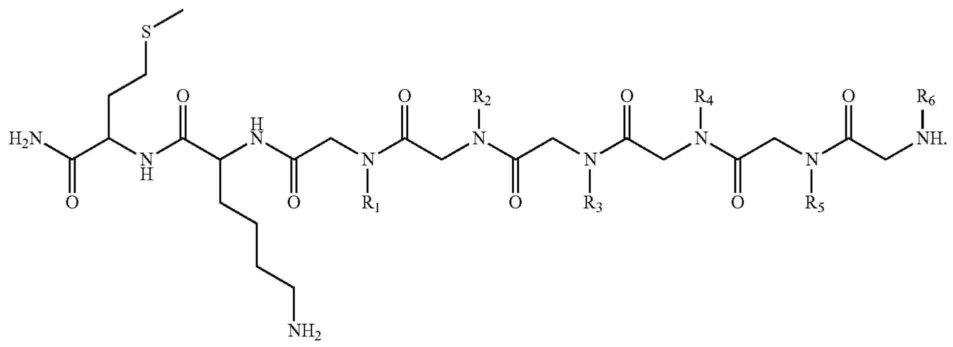

In some embodiments, $R_1$, $R_2$, $R_3$, $R_4$, $R_5$, and $R_6$ (R groups) each independently includes, without limitation, one or more of the following functional groups:

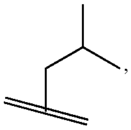 , 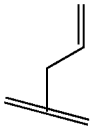 , 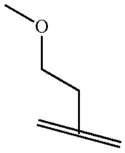 ,

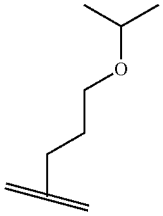 , 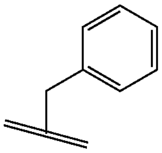 ,

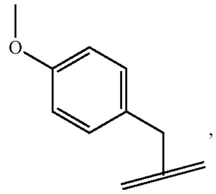 , derivatives thereof, or combinations thereof.

In some embodiments, $R_1$, $R_2$, $R_3$, $R_4$, $R_5$, and $R_6$ each independently includes, without limitation one or more of the following functional groups:

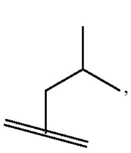 , 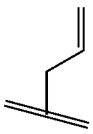 , 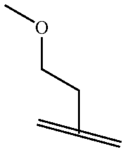 ,

-continued

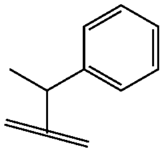 , 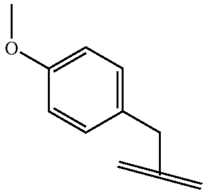 , derivatives thereof, or combinations thereof. In some embodiments, each R group end defined by // is appended directly to a corresponding N atom of the peptoid backbone.

In some embodiments, $R_1$, $R_2$, $R_3$, $R_4$, $R_5$, and $R_6$ each independently includes, without limitation one or more of the following functional groups:

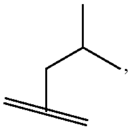 , 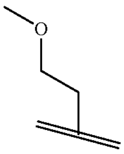 , 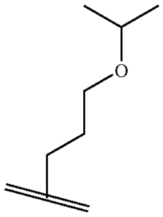 ,

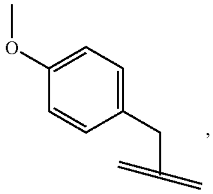 , derivatives thereof, or combinations thereof. In some embodiments, each R group end defined by // is appended directly to a corresponding N atom of the peptoid backbone.

In some embodiments, the peptoid includes the following structure or a derivative thereof:

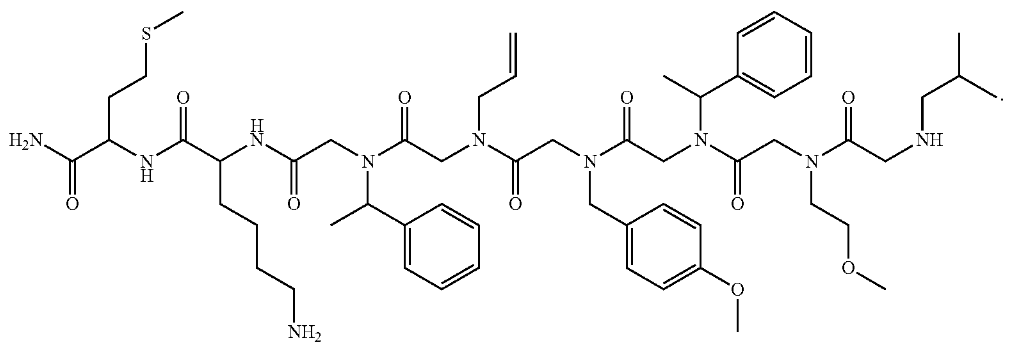 [SMILES: C=CCN(CC(=O)N(CC(=O)NC(CCCCN)C(=O)NC(CCSC)C(N)=O)C(C)c1ccccc1)C(=O)CN(Cc1ccc(OC)cc1)C(=O)CN(C(=O)CN(CCOC)C(=O)CNCC(C)C)C(C)c1ccccc1]

In some embodiments, the peptoid includes the following structure or a derivative thereof:

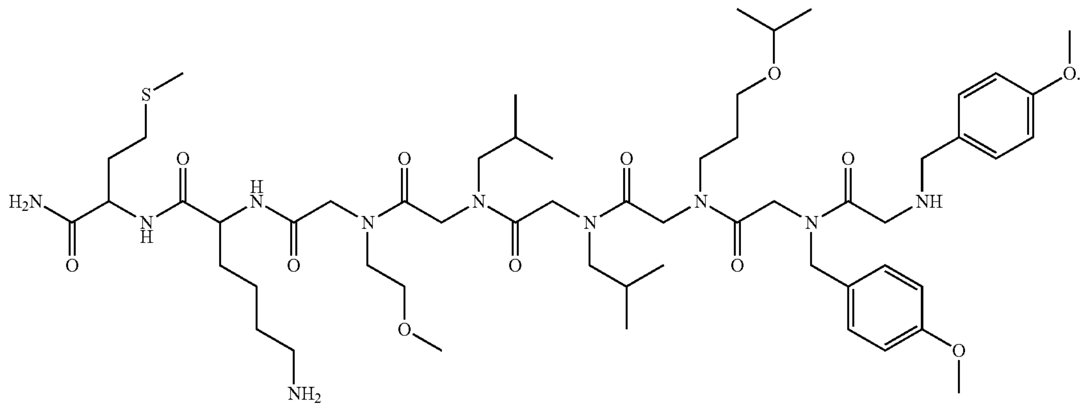 [SMILES: COCCN(CC(=O)NC(CCCCN)C(=O)NC(CCSC)C(N)=O)C(=O)CN(CC(C)C)C(=O)CN(CC(C)C)C(=O)CN(CCCOC(C)C)C(=O)CN(Cc1ccc(OC)cc1)C(=O)CNCc1ccc(OC)cc1]

In some embodiments, the peptoid includes one or more peptoid derivatives. In some embodiments, the one or more peptoid derivatives include one or more peptoid moieties derivatized with a functional group. In some embodiments, the one or more peptoid moieties are positioned on peptoid backbones, R groups, or combinations thereof.

Peptoid moieties of derivatized peptoids may be derivatized with various functional groups. For instance, in some embodiments, the functional groups include, without limitation, alkanes, alkenes, ethers, alkynes, alkoxyls, aldehydes, carboxyls, hydroxyls, hydrogens, sulfurs, phenyls, cyclic rings, aromatic rings, heterocyclic rings, linkers, or combinations thereof.

In some embodiments, the peptoid includes a multimer. In some embodiments, the peptoids in the multimer are connected through covalent linkages on peptoid backbones, R groups, or combinations thereof. In some embodiments, the covalent linkages are positioned at the C-terminus of peptoids, the N-terminus of peptoids, regions proximal to the N-terminus of peptoids, middle regions of peptoids, regions proximal to the C-terminus of peptoids, or combinations thereof. In some embodiments, the covalent linkages are positioned at the N-terminus of peptoids.

In some embodiments, the peptoids in the multimer are connected through one or more linkers. In some embodiments, the one or more linkers link peptoids through covalent linkages on peptoid backbones, R groups, or combinations thereof. In some embodiments, the one or more linkers include, without limitation, rigid linkers, semi-rigid linkers, flexible linkers, semi-flexible linkers, cleavable linkers, non-cleavable linkers, lysine-based linkers, glycine-based linkers, cyclic linkers, heterocyclic linkers, alicyclic linkers, non-cyclic linkers, aliphatic linkers, aromatic linkers, sulfide-based linkers, ester-based linkers, ether-based linkers, polyethylene glycol-based linkers, glycol-based linkers, allyl-based linkers, benzyl-based linkers, amino hexanoic-based linkers, NHS ester-based linkers, maleimide-based linkers, and combination thereof.

In some embodiments, the multimer includes, without limitation, a homomultimer, a heteromultimer, a cyclic multimer, a dimer, a trimer, a tetramer, or combinations thereof. In some embodiments, the peptoid is in the form of a dimer, a trimer, or a tetramer. In some embodiments, the peptoid is in the form of a homo-multimer, such as a homodimer, homotrimer, or homotetramer. In some embodiments, the peptoid is in the form of a hetero-multimer, such as a heterodimer, heterotrimer, or heterotetramer.

In some embodiments, the peptoid includes the following structure or a derivative thereof:
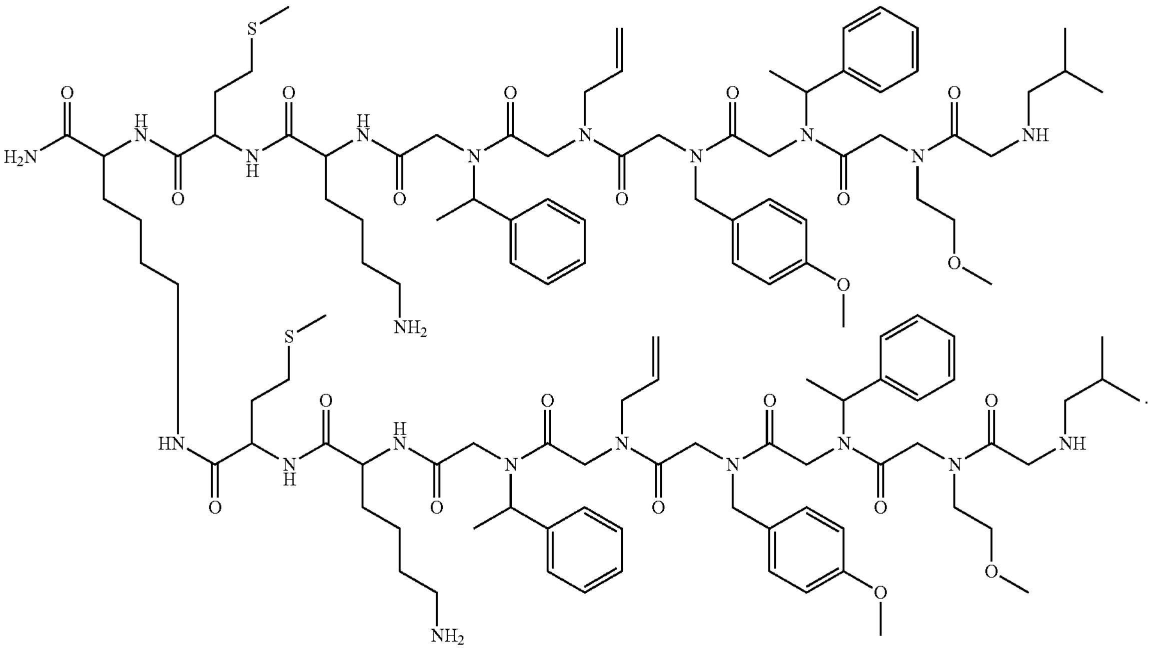 [SMILES: C=CCN(CC(=O)N(CC(=O)NC(CCCCN)C(=O)NC(CCSC)C(=O)NCCCCC(NC(=O)C(CCSC)NC(=O)C(CCCCN)NC(=O)CN(C(=O)CN(CC=C)C(=O)CN(Cc1ccc(OC)cc1)C(=O)CN(C(=O)CN(CCOC)C(=O)CNCC(C)C)C(C)c1ccccc1)C(C)c1ccccc1)C(N)=O)C(C)c1ccccc1)C(=O)CN(Cc1ccc(OC)cc1)C(=O)CN(C(=O)CN(CCOC)C(=O)CNCC(C)C)C(C)c1ccccc1]
In some embodiments, the peptoid includes the following structure or a derivative thereof:
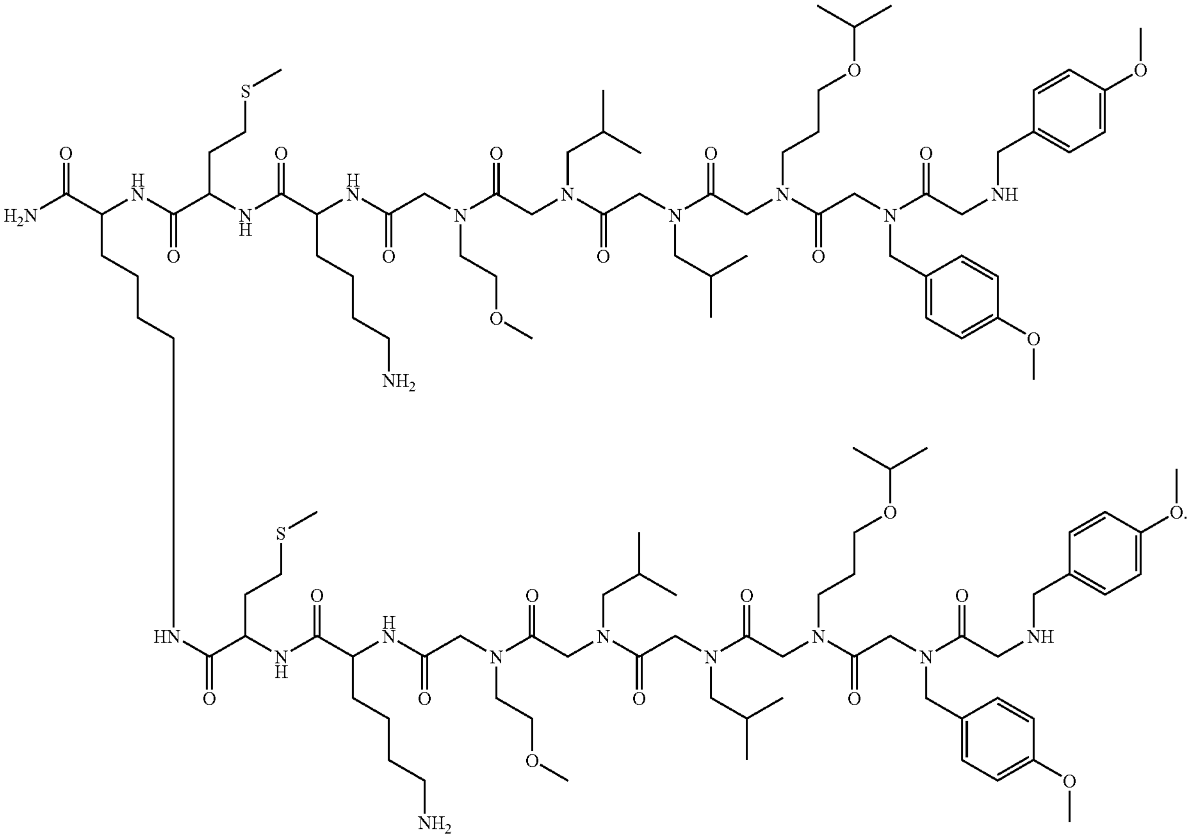

In some embodiments, the peptoid includes the following structure or a derivative thereof:
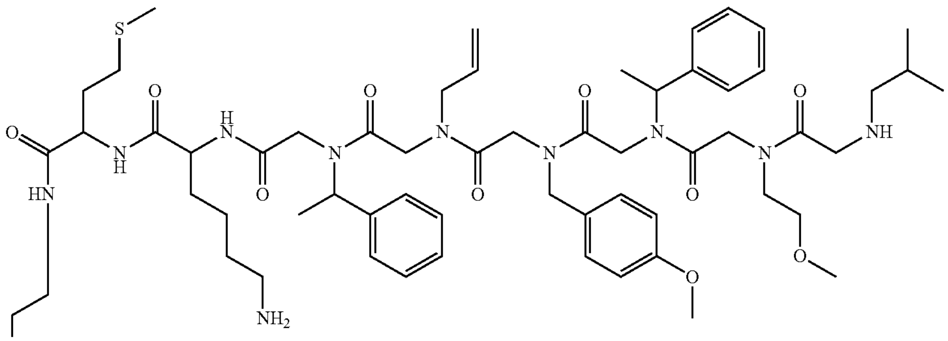
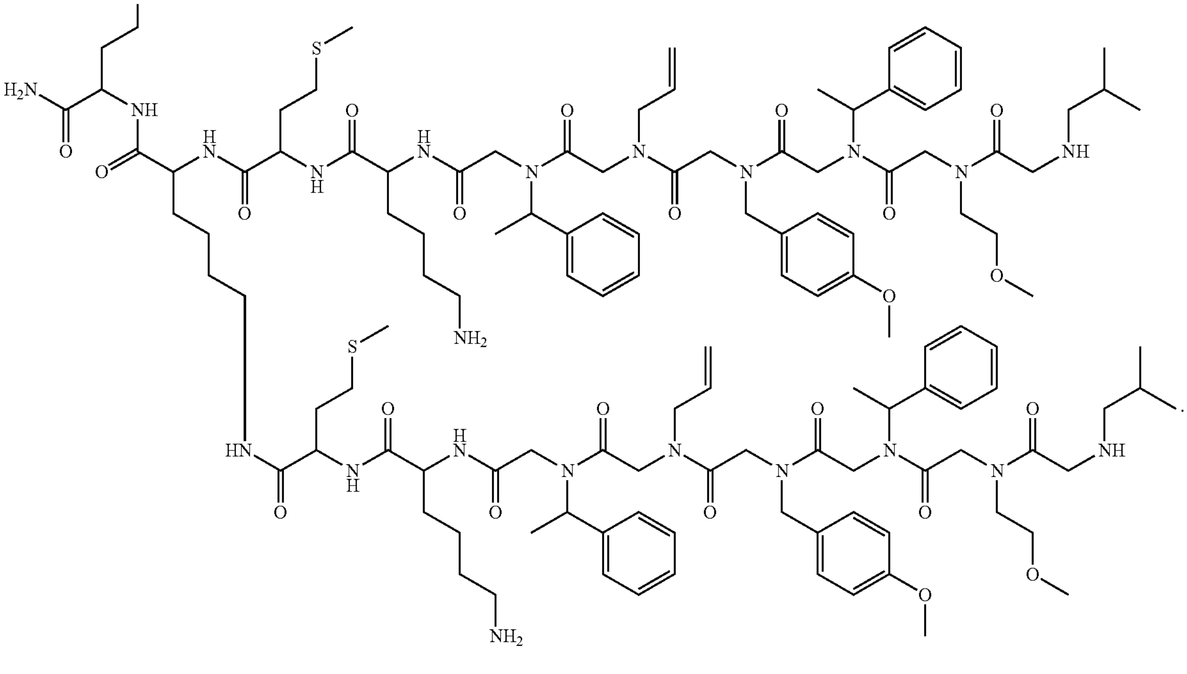
.

In some embodiments, the peptoid includes the following structure or a derivative thereof:
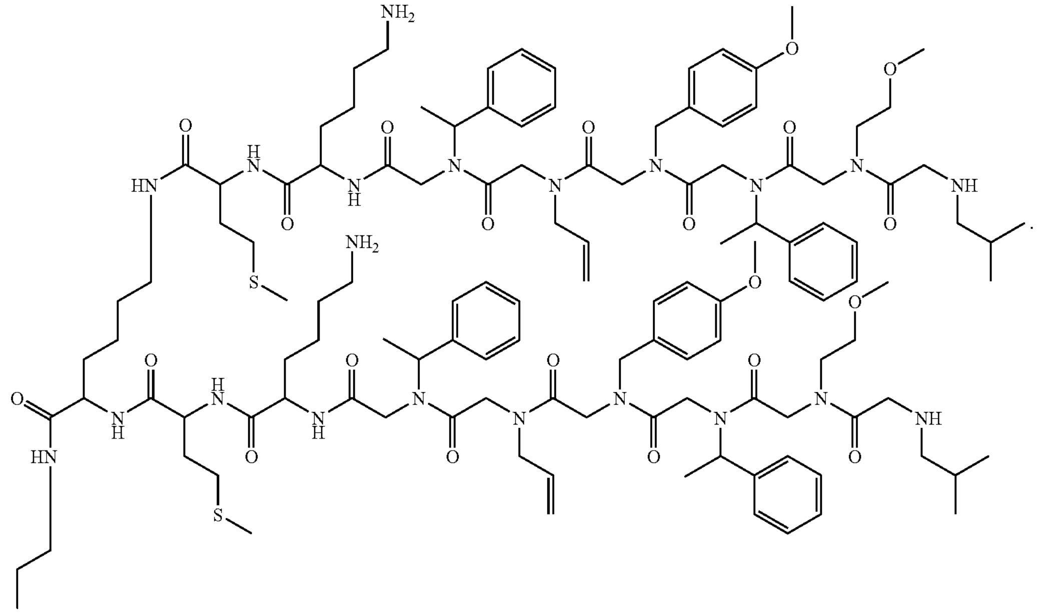
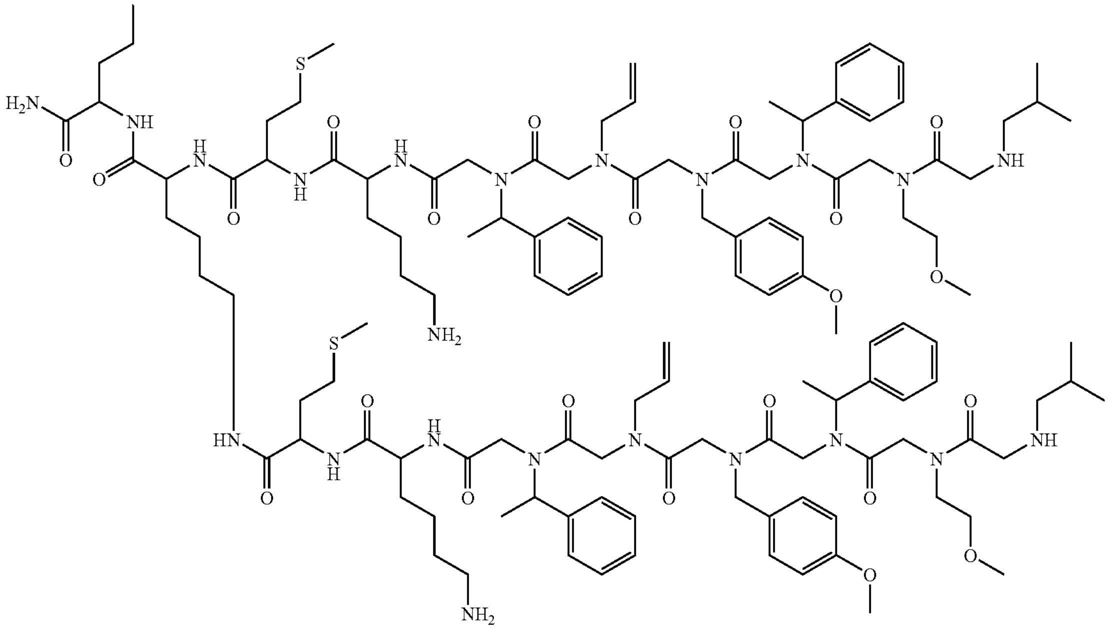

In some embodiments, the peptoid includes the following structure or a derivative thereof:
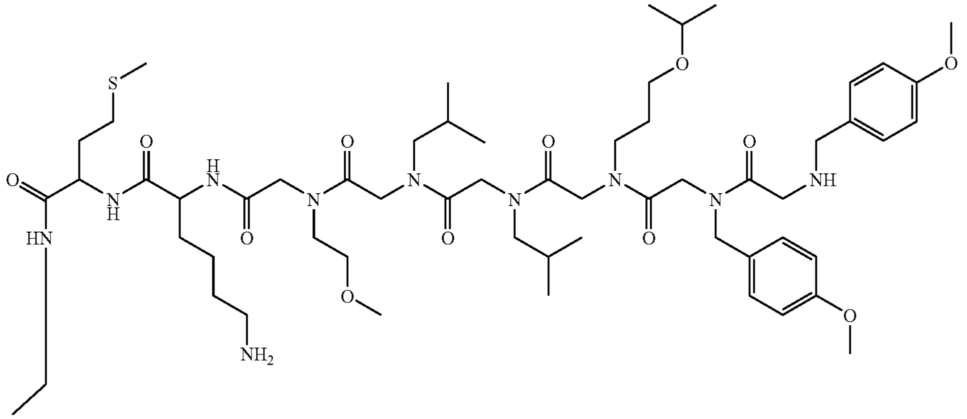
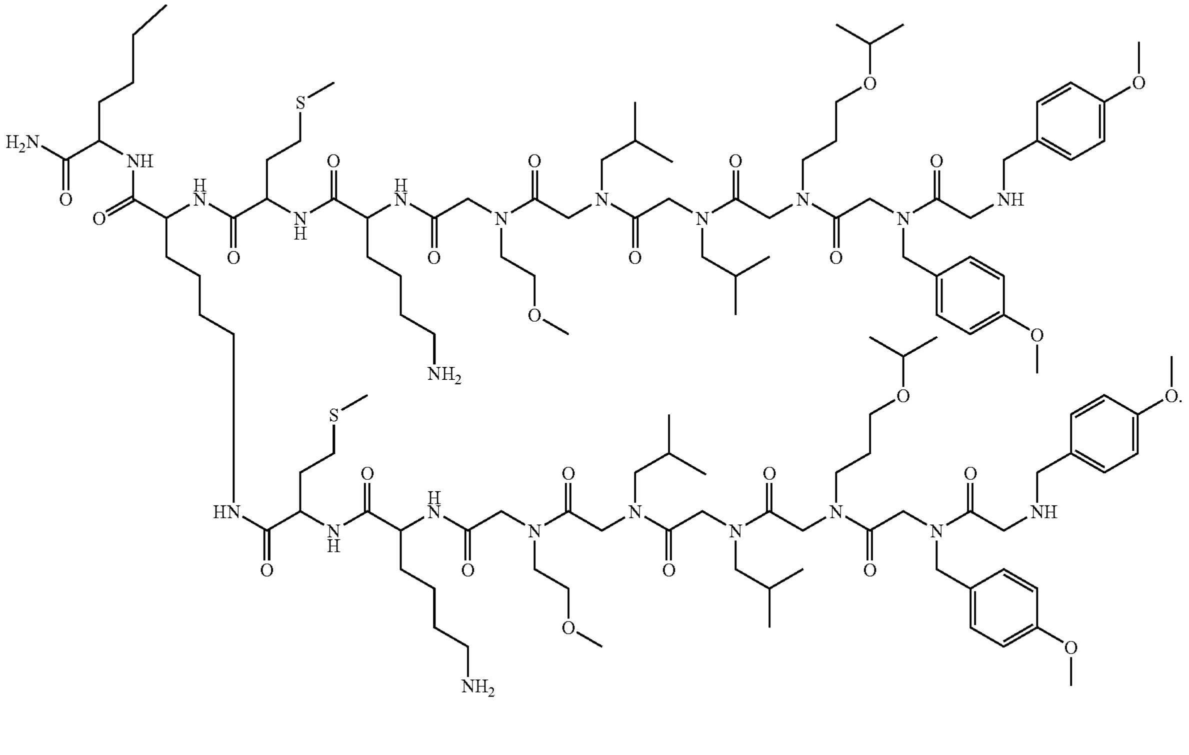

In some embodiments, the peptoid includes the following structure or a derivative thereof:

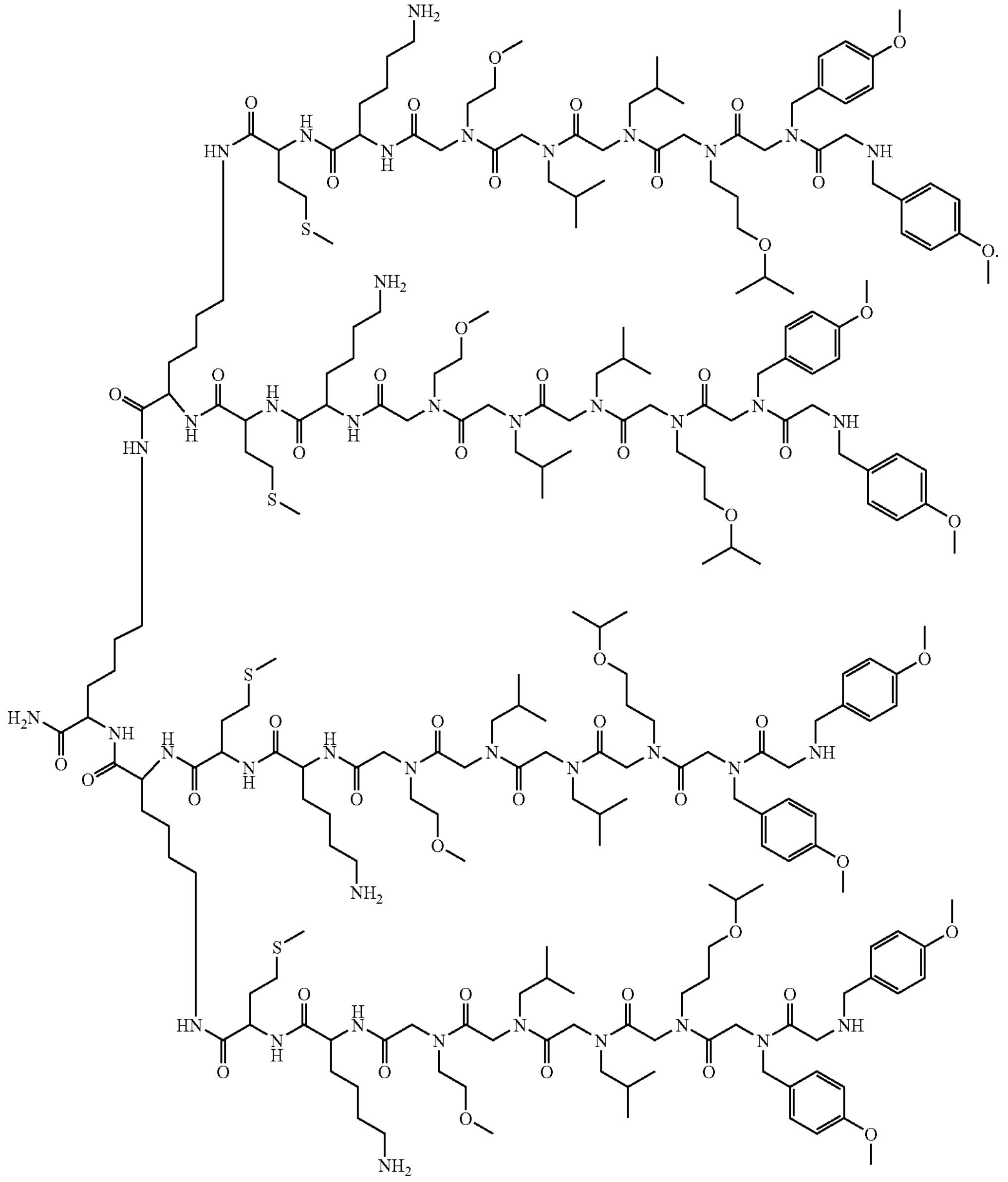

The peptoids of the present disclosure can be in various compositions. For instance, in some embodiments, the peptoids of the present disclosure are in therapeutic compositions.

The compositions of the present disclosure can be in various forms. For instance, in some embodiments, the compositions of the present disclosure are in the form of nasal sprays, eye drops, injectable suspensions, tablets, or combinations thereof.

In some embodiments, the compositions of the present disclosure can be in the form of particles. For instance, in some embodiments, the compositions of the present disclosure include lipid-based particles, carbon-based particles, metal-based particles, and combinations thereof. In some embodiments, the particles of the present disclosure are in the form of nanoparticles. In some embodiments, the peptoids of the present disclosure are encapsulated within the particles of the present disclosure.

In some embodiments, the compositions of the present disclosure also include one or stabilizers. In some embodiments, the stabilizers include, without limitation, anti-oxidants, sequestrants, ultraviolet stabilizers, and combinations thereof.

In some embodiments, the compositions of the present disclosure also include one or more surfactants. In some embodiments, the surfactants include, without limitation, anionic surfactants, cationic surfactants, zwitterionic surfactants, non-ionic surfactants, and combinations thereof.

In some embodiments, the compositions of the present disclosure also include one or more excipients. In some embodiments, the excipients include, without limitation, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, polyvinyl alcohol, or combinations thereof.

In some embodiments, the compositions of the present disclosure are in a form that is suitable for use as a nasal spray. In some embodiments, the compositions of the present disclosure are in a form that is suitable for use as an eye drop.

Prevention of Virus Entry into Cells

The peptoids of the present disclosure can be utilized to prevent the entry of various viruses into cells. For instance, in some embodiments, the virus includes a virus that is capable of entering cells through the angiotensin-converting enzyme 2 (ACE2) receptor.

In some embodiments, the virus includes a coronavirus. In some embodiments, the coronavirus includes, without limitation, severe acute respiratory syndrome coronavirus (SARS-CoV), severe acute respiratory syndrome-related coronavirus (SARSr-COV), human coronavirus 229E (HCoV-229E), human coronavirus NL63 (HCoV-NL63), human coronavirus OC43 (HCoV-OC43), human coronavirus HKU1 (HCoV-HKU1), Middle East respiratory syndrome-related coronavirus (MERS-COV), severe acute respiratory syndrome-related coronavirus 2 (SARS-CoV-2), or combinations thereof. In some embodiments, the virus is SARS-CoV-2.

Figure 2:
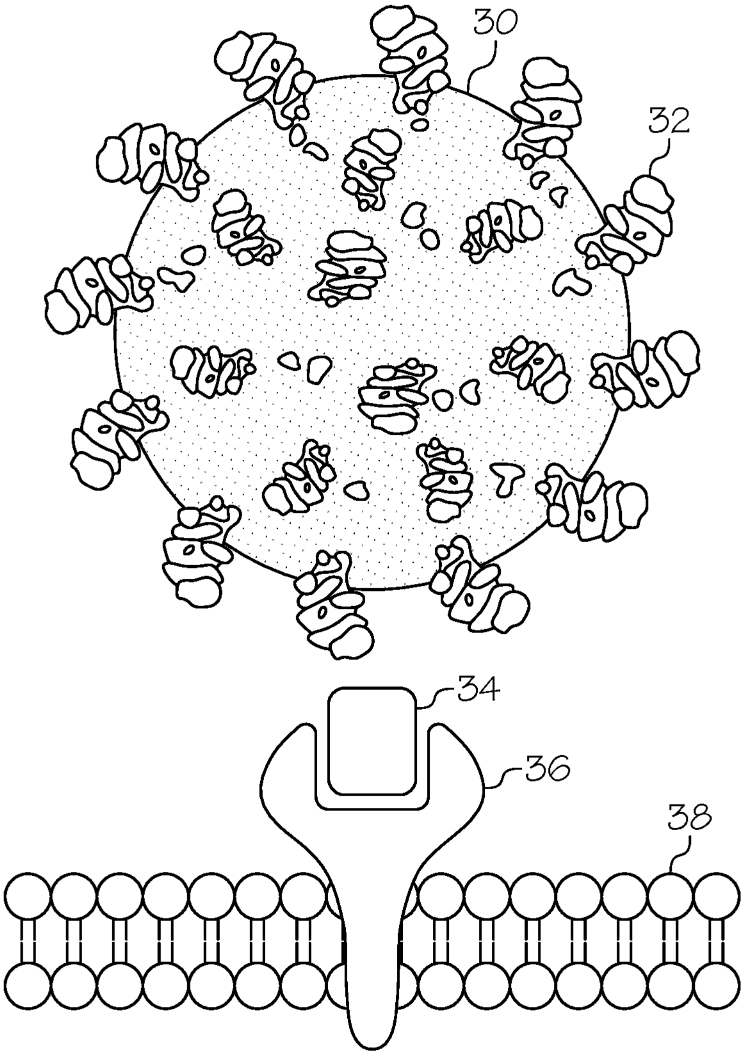
FIG. 2 illustrates a mechanism by which anti-viral peptoids block virus entry into cells.

Without being bound by theory, the peptoids of the present disclosure can block the entry of viruses into cells through numerous mechanisms. For instance, in some embodiments illustrated in FIG. 2, the peptoids of the present disclosure (e.g., peptoid 34) block entry of a virus (e.g., virus 30) into cells (e.g., cells 38) by binding to angiotensin-converting enzyme 2 receptors (e.g., receptor 36) on the cells.

The peptoids of the present disclosure may bind to various domains of ACE 2 receptors. For instance, in some embodiments, the binding occurs on an enzymatic domain of ACE 2 receptors. In some embodiments, the binding occurs on a virus protein binding domain of ACE 2 receptors. In some embodiments, the virus binding protein is a spike glycoprotein (S protein).

The peptoids of the present disclosure may bind to various types of ACE 2 receptors. For instance, in some embodiments, the ACE 2 receptors are human ACE 2 receptors. In some embodiments, the ACE receptors are feline ACE 2 receptors. In some embodiments, the ACE 2 receptors are canine ACE 2 receptors.

The peptoids of the present disclosure may block virus entry into cells in various manners. For instance, in some embodiments, the peptoids of the present disclosure block the entry of viruses into cells without affecting the enzymatic activity of the ACE 2 receptors.

Association of Anti-Viral Peptoids and Compositions with Cells

The peptoids and compositions of the present disclosure can be associated with various types of cells. For instance, in some embodiments, the cells include, without limitation, endothelial cells, epithelial cells, or combinations thereof.

In some embodiments, the association of the peptoids and compositions of the present disclosure occurs in vitro. In some embodiments, the association occurs in vivo. In some embodiments, the association occurs in vivo in a subject. In some embodiments, the association occurs in vivo in a subject through the administration of the peptoids and compositions of the present disclosure to the subject.

In some embodiments, the administration occurs by intravenous administration. In some embodiments, the administration occurs by nasal administration. In some embodiments, the administration occurs by ocular administration. In some embodiments, the administration occurs by inhalation. In some embodiments, the administration occurs by oral administration.

Subjects

The peptoids and compositions of the present disclosure may be administered to various subjects. For instance, in some embodiments, the subject is a human being. In some embodiments, the subject is an animal, such as a domesticated animal. In some embodiments, the domesticated animal includes, without limitation, cats, dogs, sheep, horses, cows, or combinations thereof.

In some embodiments, the subject is suffering from a viral infection. In some embodiments, the subject is vulnerable to a viral infection.

In some embodiments, the peptoids, compositions and methods of the present disclosure can be utilized to treat a viral infection in a subject. In some embodiments, the peptoids, compositions, and methods of the present disclosure can be utilized to prevent a viral infection in a subject. In some embodiments, the viral infection is caused by a coronavirus, such as SARS-CoV-2.

Applications and Advantages

The present disclosure can have various advantages. For instance, in some embodiments, the anti-viral peptoids of the present disclosure can block the entry of viruses into human cells through the ACE2 receptor without affecting ACE2 enzymatic activity, which is important in maintaining normal blood pressure. In contrast, prior molecules that targeted ACE2 receptors (e.g., antibodies) interfered with ACE2 enzymatic activity. As such, the anti-viral peptoids of the present disclosure can be utilized in accordance with the methods of the present disclosure to treat and prevent viral infections without having side effects, such as side effects related to the maintenance of blood pressure.

Additionally, due to their peptoid-based structure, the anti-viral peptoids of the present disclosure can have optimal pharmacokinetic properties. In particular, peptoids closely resemble peptides except that their side chains extend from the main chain nitrogen rather than from the α-carbon. Due to such structural differences, peptoids are protease-resistant, highly tissue-permeable, serum stable, orally available, and non-immunogenic.

Therefore, the anti-viral peptoids of the present disclosure provide higher stability, better tissue permeability, and higher shelf-life when compared to current anti-viral drugs, such as small molecules, peptides and antibodies. For instance, the anti-viral peptoids of the present disclosure can be effectively administered to subjects in accordance with the methods of the present disclosure through numerous routes, such as through nasal administration, ocular administration, and oral administration.

Additionally, due to the availability of high throughput peptoid synthesis technologies, the anti-viral peptoids of the present disclosure can be manufactured in an efficient, economical and cost effective manner. This in turn can reduce anti-viral treatment costs.

In view of the aforementioned advantages, the anti-viral peptoids, compositions, and methods of the present disclosure can have numerous applications. For instance, since the ACE2 receptor is critical for SARS-CoV-2 entry into human cells, the anti-viral peptoids of the present disclosure can be utilized in accordance with the methods of the present disclosure to treat or prevent COVID-19 and other related diseases, such as MERS and SARS. In more specific embodiments, the anti-viral peptoids of the present disclosure can be utilized in accordance with the methods of the present disclosure to treat SARS-CoV-2 positive patients by blocking the entry of newly amplified viruses into more cells. In some embodiments, the anti-viral peptoids of the present disclosure can be utilized in accordance with the methods of the present disclosure to prevent SARS-CoV-2 infections in patients by blocking the entry of introduced viruses into cells.

The use of the anti-viral peptoids, compositions, and methods of the present disclosure to treat or prevent COVID-19 provides an unmet need because the COVID-19 pandemic currently represents a global health crisis. While vaccines have become available for preventing COVID-19, preventive drugs will be extremely important in long-term applications because vaccines may not offer long term protection, as recent reports suggest that COVID-19 patients quickly lose the antibodies after infection.

ADDITIONAL EMBODIMENTS

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Novel Peptoid Compounds that Bind to ACE2 Receptor and Prevent SARS-CoV-2 Virus Entry into Human Cells The SARS-CoV-2 coronavirus has been causing the COVID-19 pandemic, which has become the biggest health crisis in recent history. In order to enter the human body, the SARS-CoV-2 virus uses its spike protein to bind to the human angiotensin-converting enzyme 2 (ACE2) protein, which allows the entry of the virus. Thus, the interaction between the receptor-binding domain of the spike glycoprotein (S protein) of SARS-CoV-2 and the peptidase domain of ACE2 is the key for virus infection.

Using unique on-bead two-color combinatorial cell-screening technology (OBTC), Applicant discovered two new peptoid (oligo-N-substituted glycine) compounds (ACE2P1, ACE2P2) that specifically bind to the ACE2 protein. Applicant has shown that both ACE2P1 and ACE2P2 bind to ACE2 expressing cells, but not the cells that do not have ACE2. More importantly, both ACE2P1 and ACE2P2 can block the binding of SARS-CoV-2 spike protein binding to the ACE2 protein in an in vitro pull-down assay.

The data suggest that both compounds can potentially block the entry of SARS-CoV-2 into human cells. Furthermore, ACE2 is an important enzyme that maintains normal blood pressure. Applicant's data indicates that ACE2P1 and ACE2P2 do not inhibit this ACE2 enzyme activity, suggesting that these compounds will not have side effects affecting the maintenance of the blood pressure.

Example 1.1. Peptoids as Better Therapeutic Agents

Figure 3A:
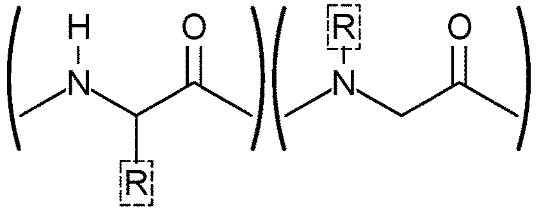
FIGS. 3A and 3B illustrate anti-viral peptoid development.
Figure 3B:
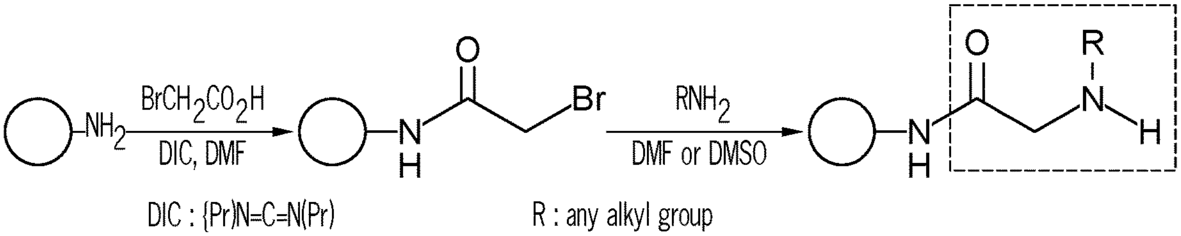

Peptoids (oligo-N-substituted glycines) closely resemble peptides except that their side chains extend from the main chain nitrogen rather than from the α-carbon (FIG. 3A). These oligomers are achiral, protease-resistant, and highly tissue-permeable. The synthesis of peptoids is straightforward since adding one residue (equivalent to a peptide amino acid) requires only two chemical steps, which can be completed by two, 15-second microwave pulses (FIG. 3B).

Peptoids are rich sources of protein-binding ligands and are non-immunogenic in mice. Furthermore, peptoid modifications are straightforward and have moderate clearance.

Example 1.2. Unique On-Bead Two-Color Combinatorial Cell-Screening Technology (OBTC)

Applicant previously developed an on-bead two-color combinatorial cell-screening technology (OBTC) that can identify high specific chemical compounds for a receptor found in one cell surface over another control cell surface that is missing the receptor. This technology guarantees the identification of new synthetic compounds that only recognize the targeted receptor and do not bind to thousands of other cell surface receptors and molecules found on normal cells. Applicant previously identified and validated peptoid compounds (oligo-N-substituted glycine) for VEGFR2, T-cell receptors, lipid-phosphatidylserine, plectin, vimentin, IL-15, transferrin and EphB2.

Example 1.3. Utilization of OBTC to Prepare ACE2 Binding Peptoids

Figure 4:
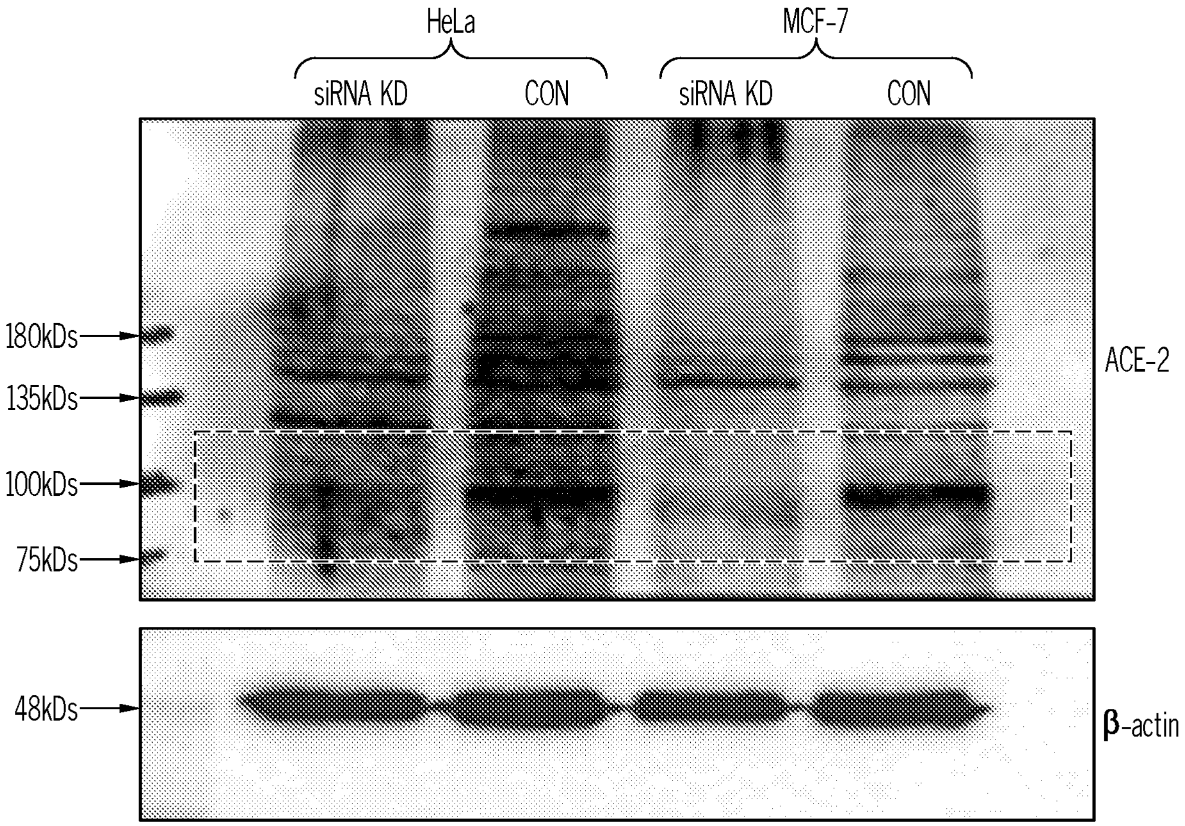
FIG. 4 provides experimental results illustrating that MCF-7 cells express ACE2, and that siRNA effectively decreases ACE2 expression. MCF-7 and HeLa cells were transfected with ACE2 targeting siRNA. ACE2 expression was detected by western blot.

In utilizing OBTC, Applicant aimed to have a cell pair that differs only by human ACE2 receptor expression. Applicant used western blot to examine ACE2 expression in cell lines and used ACE2 specific siRNA to knockdown the expression of ACE2 in ACE2 expressing cells. As shown in FIG. 4, Applicant found that MCF-7 cells express ACE2 and siRNA transfection decreases the ACE2 protein to very low levels.

Figure 5A:
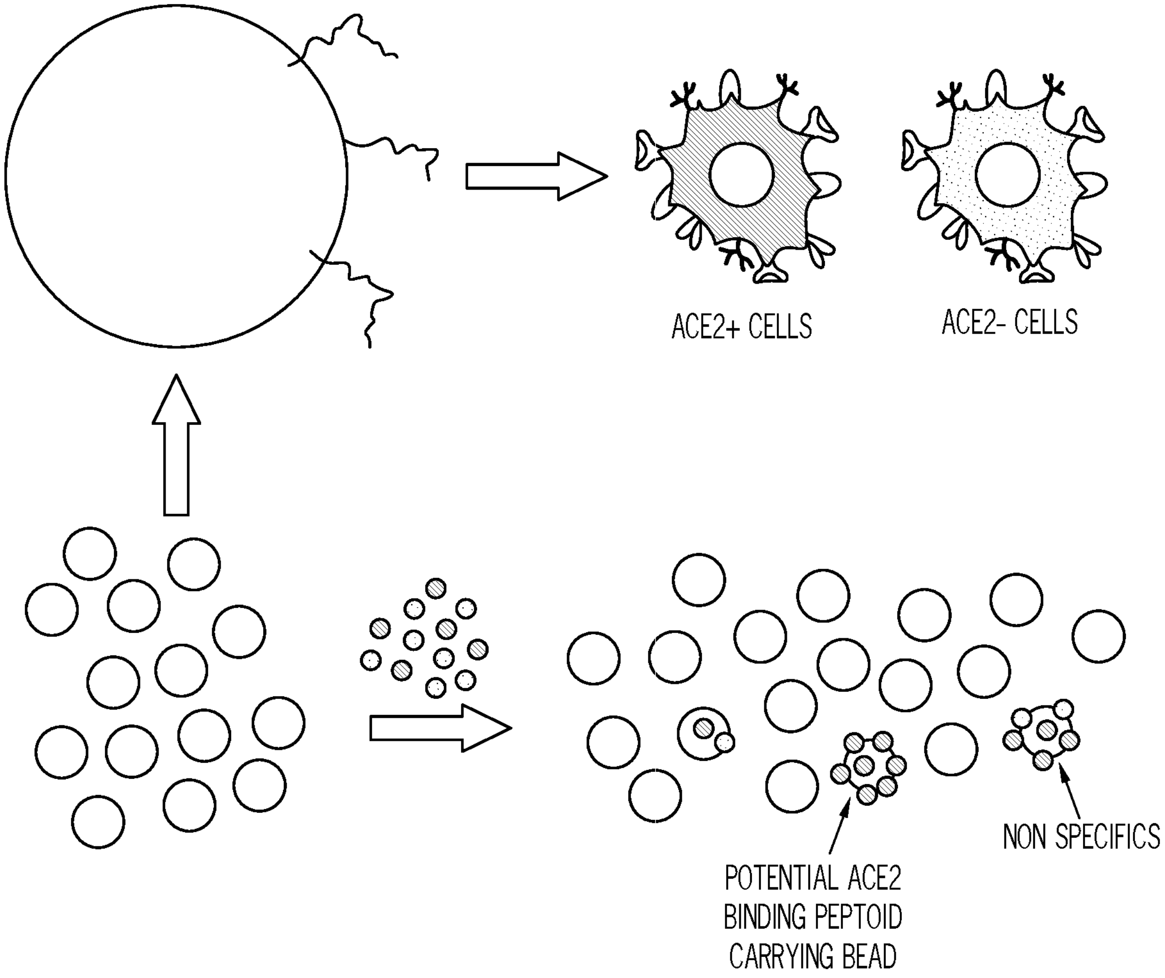
FIGS. 5A-E illustrate that an on-bead two-color combinatorial cell-screening technology (OBTC) peptoid screen identified two potential human ACE2 binding peptoids.
Figure 5B:
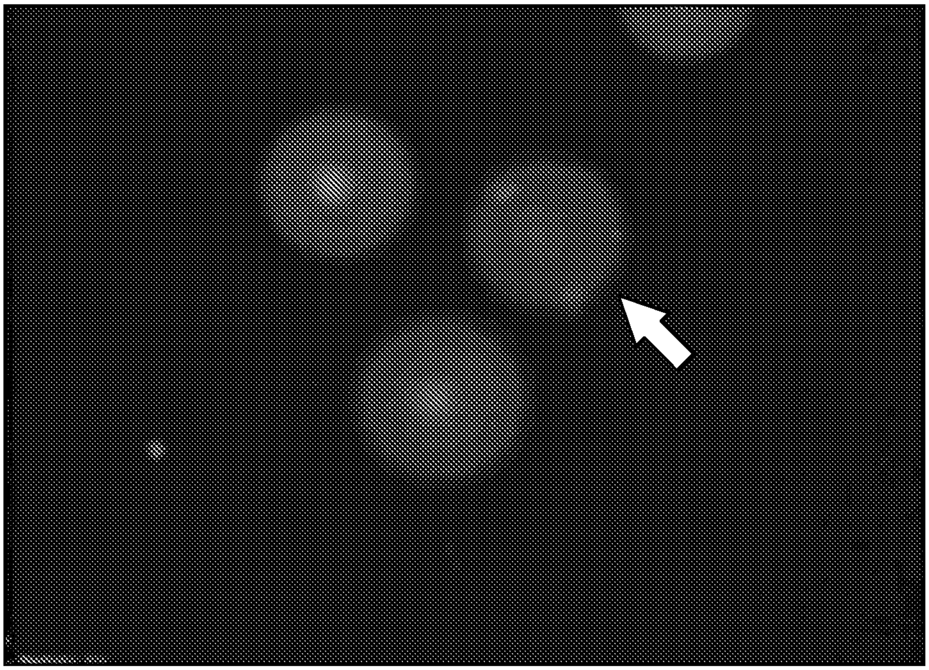
Figure 5C:
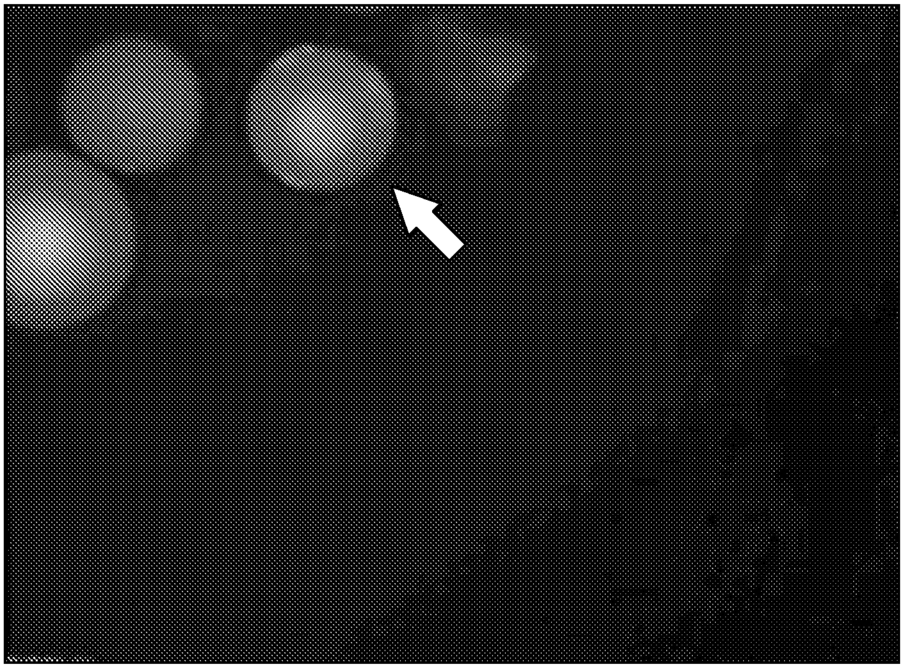
Figure 5D:
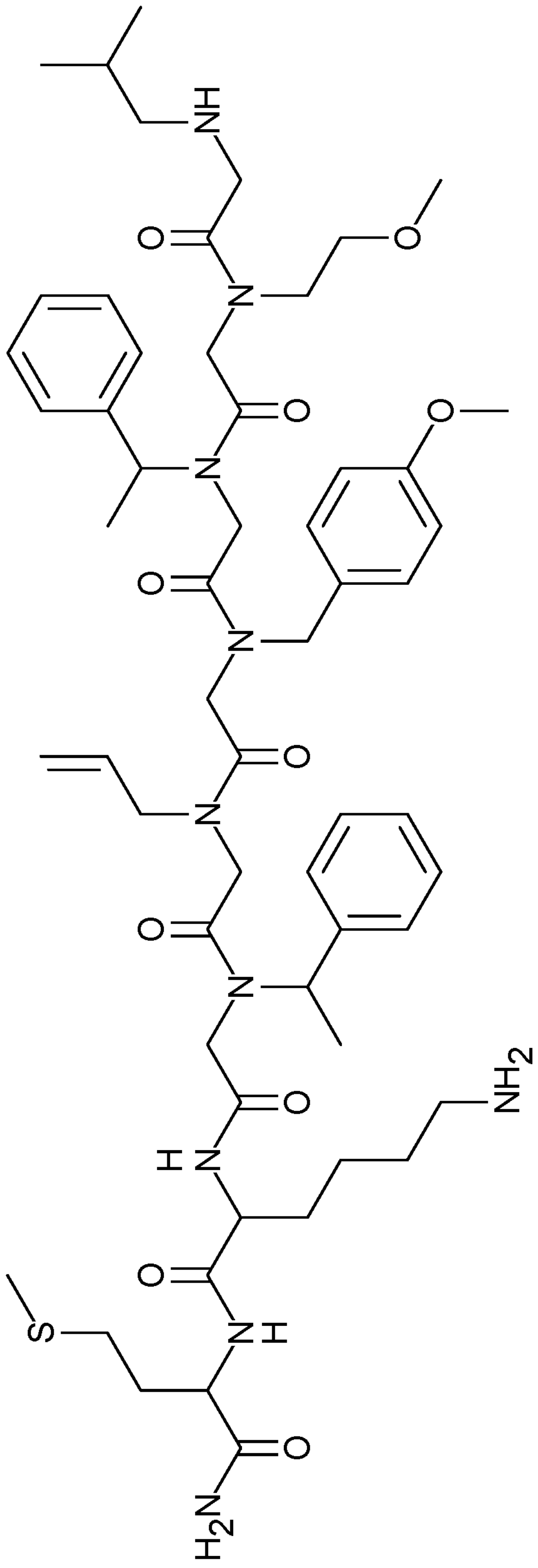
Figure 5E:
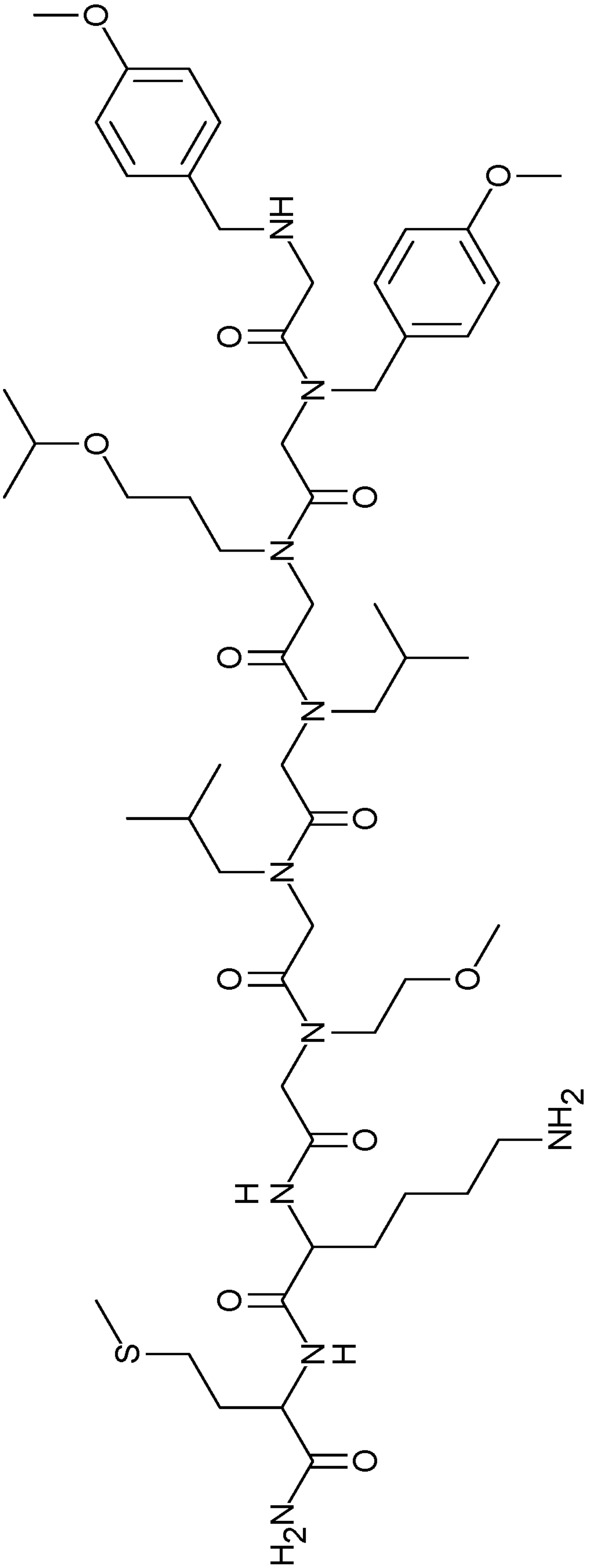

Applicant applied the OBTC technology by equilibrating human ACE2+ (red stained) and ACE2 (green stained) MCF-7 cells at 1:1 ratio on a 50,000 peptoid library, where each resin bead contain a unique peptoid sequence with lot of copies (FIG. 5A). Applicant picked only red stained cells bound beads as high potential ACE2-binding peptoid-carrying beads. Applicant found two potential hits (FIGS. 5B and 5C). Thereafter, MALDI-MS/MS sequencing identified the chemical structures (FIGS. 5D and 5E). Applicant named these two new peptoid compounds as ACE2P1 and ACE2P2.

Figure 6:
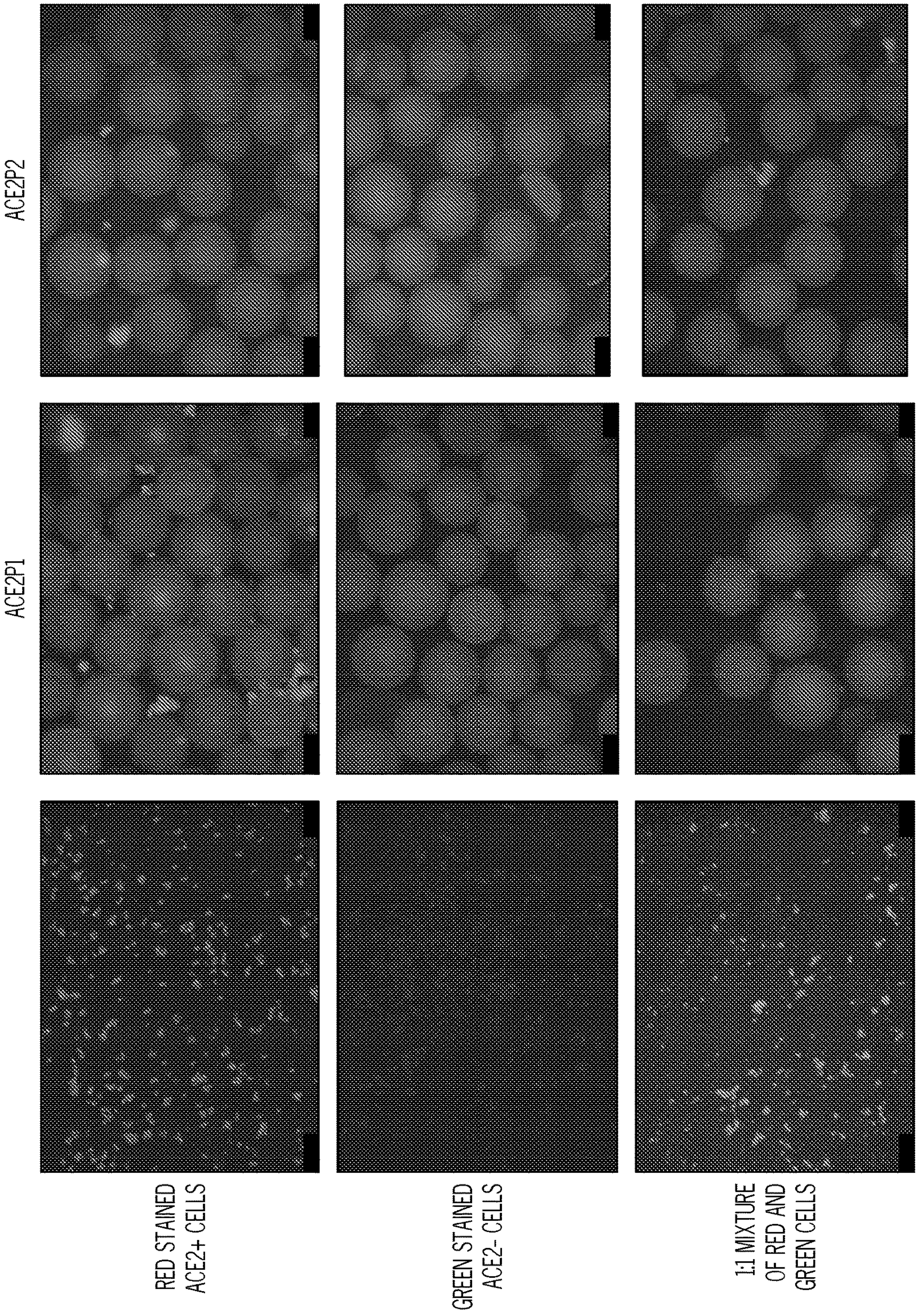
FIG. 6 provides experimental results illustrating that on-bead peptoids ACE2P1 and ACE2P2 bind to human ACE2 positive cells. The compounds ACE2P1 and ACE2P2 were resynthesized on the tentagel bead and incubated with ACE2 expressing MCF-7 cells (red stained) and ACE2 negative MCF-7 cells (green stained) individually as well as 1:1 mixture of red and green cells. Beads only showed binding with red cells but not with green cells, indicating ACE2P1 and ACE2P2 binds to human ACE2 protein.
Figure 7A:
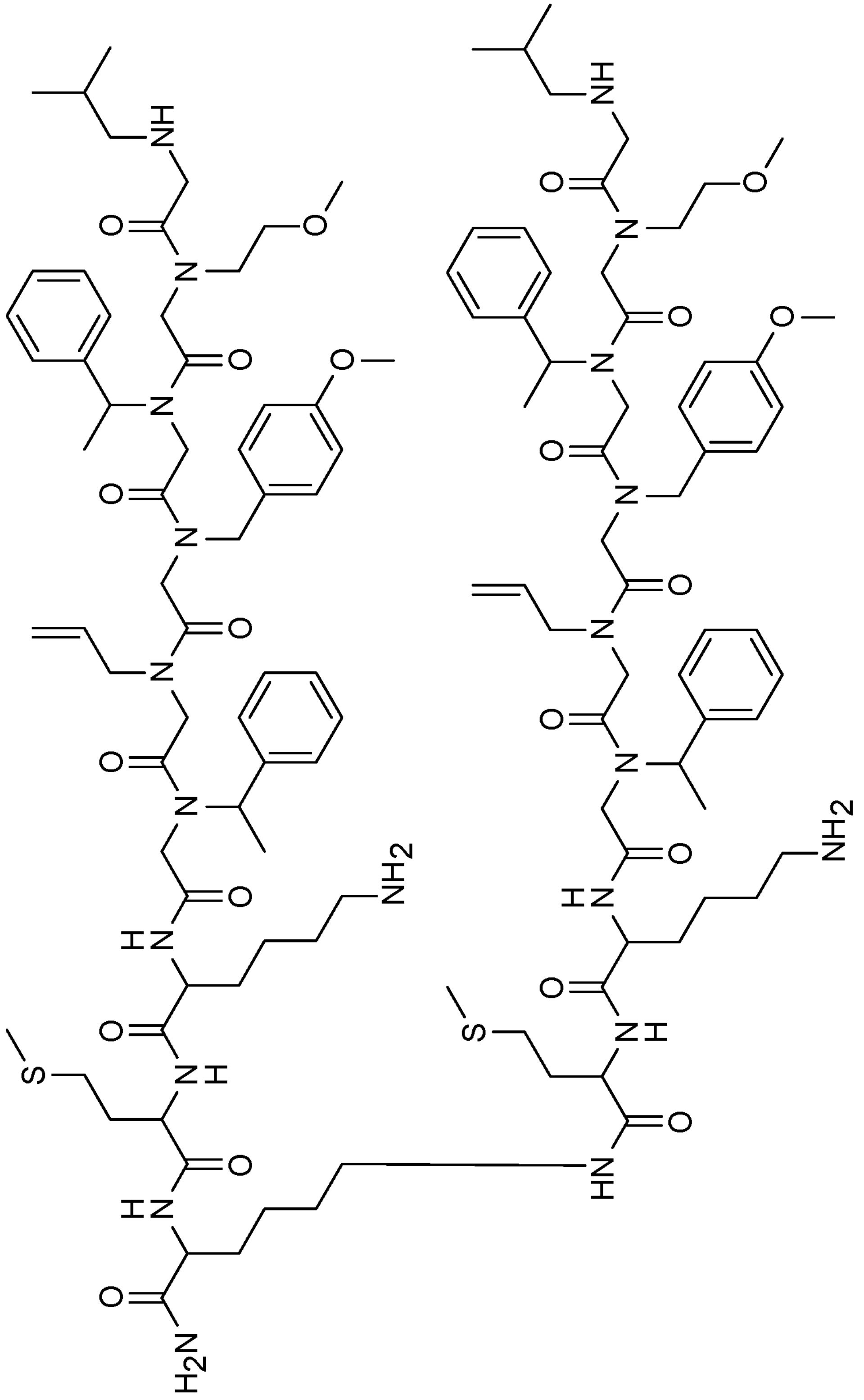
FIGS. 7A-F show homo-dimeric, -trimeric and -tetrameric derivatives of ACE2P1 and ACE2P2. The central lysine residues hold two, three and four units of monomeric versions of each peptoid ACE2P1 and ACE2P2.
Figure 7B:
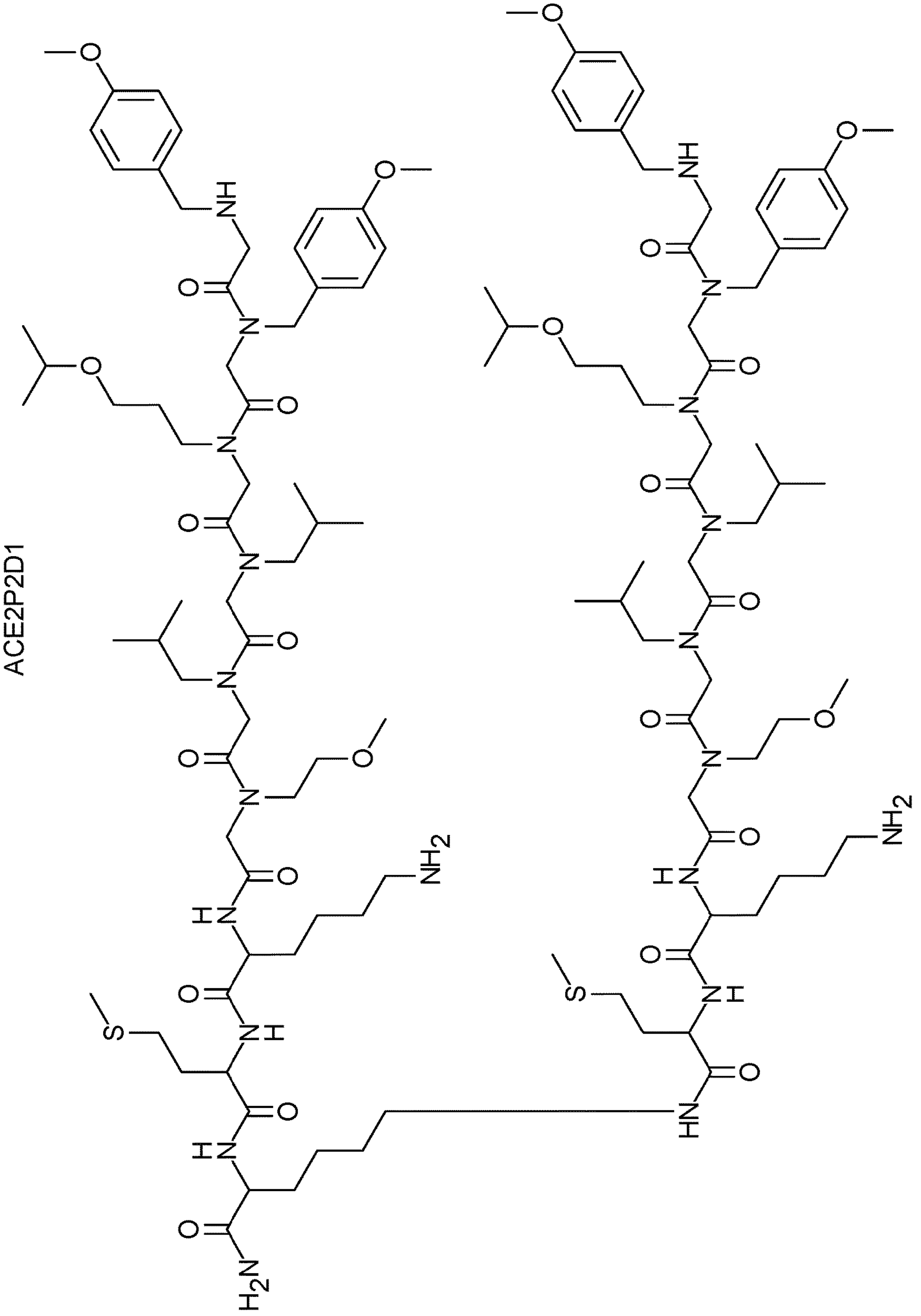
Figure 7C:
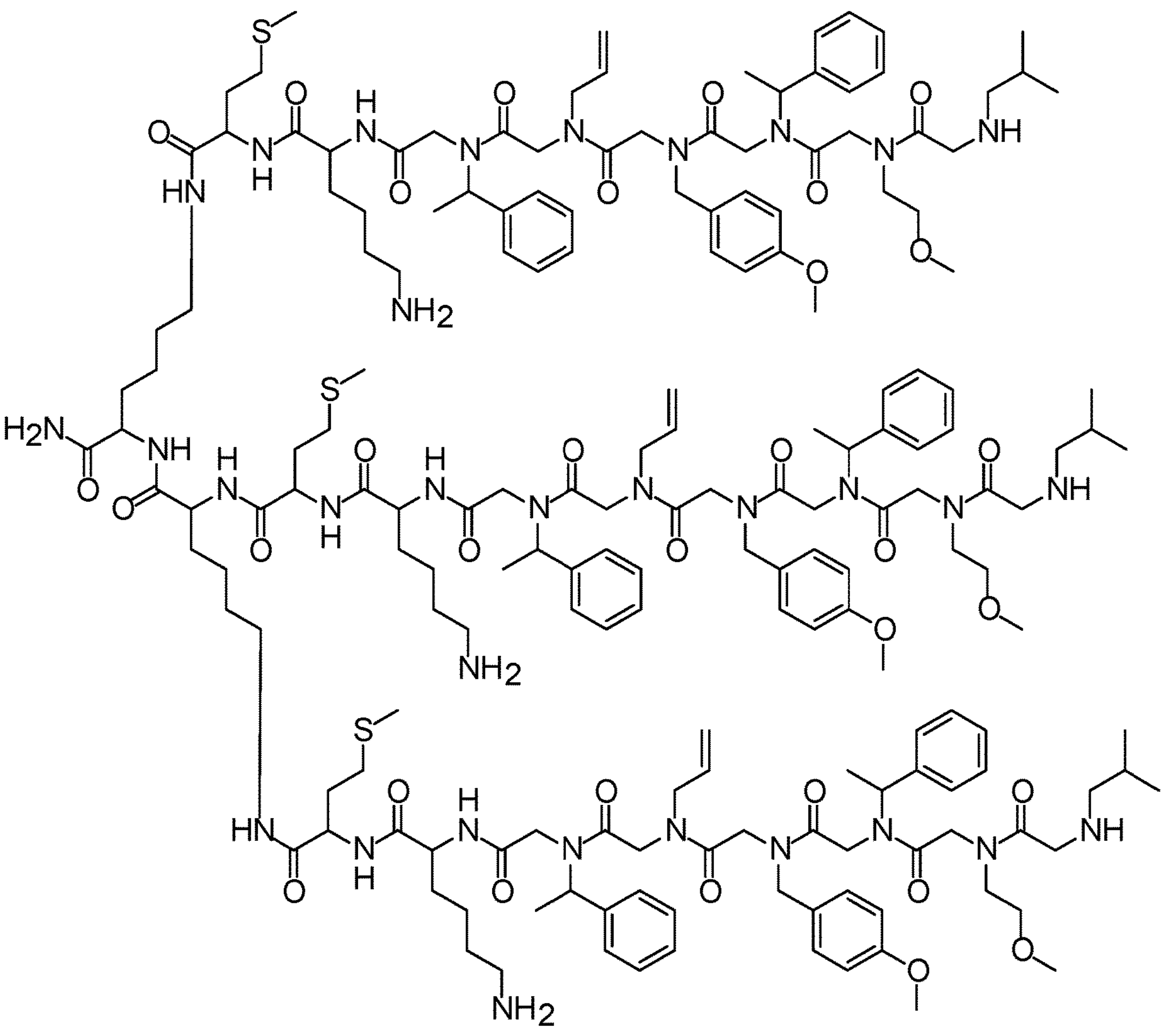
Figure 7D:
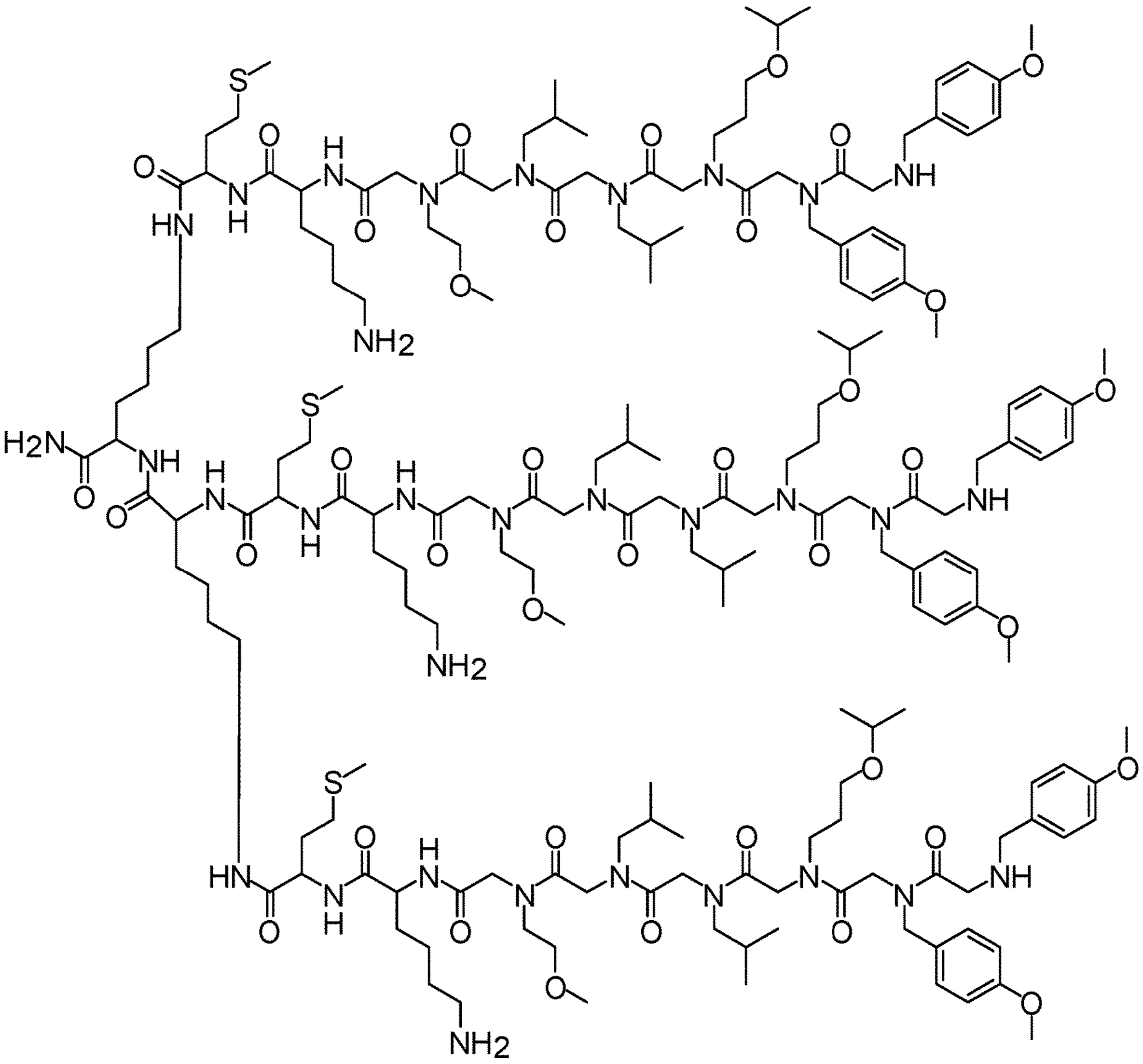
Figure 7E:
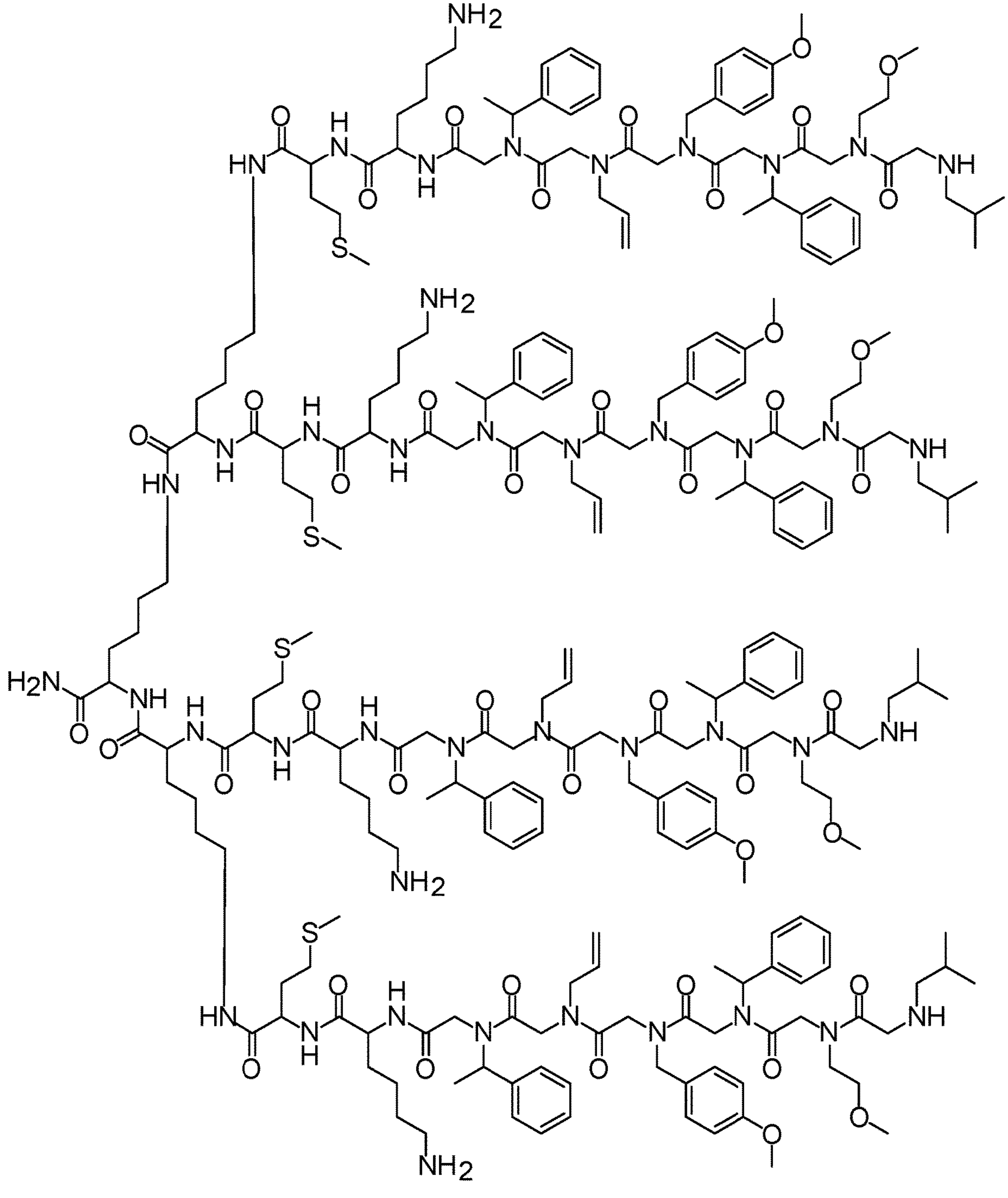
Figure 7F:
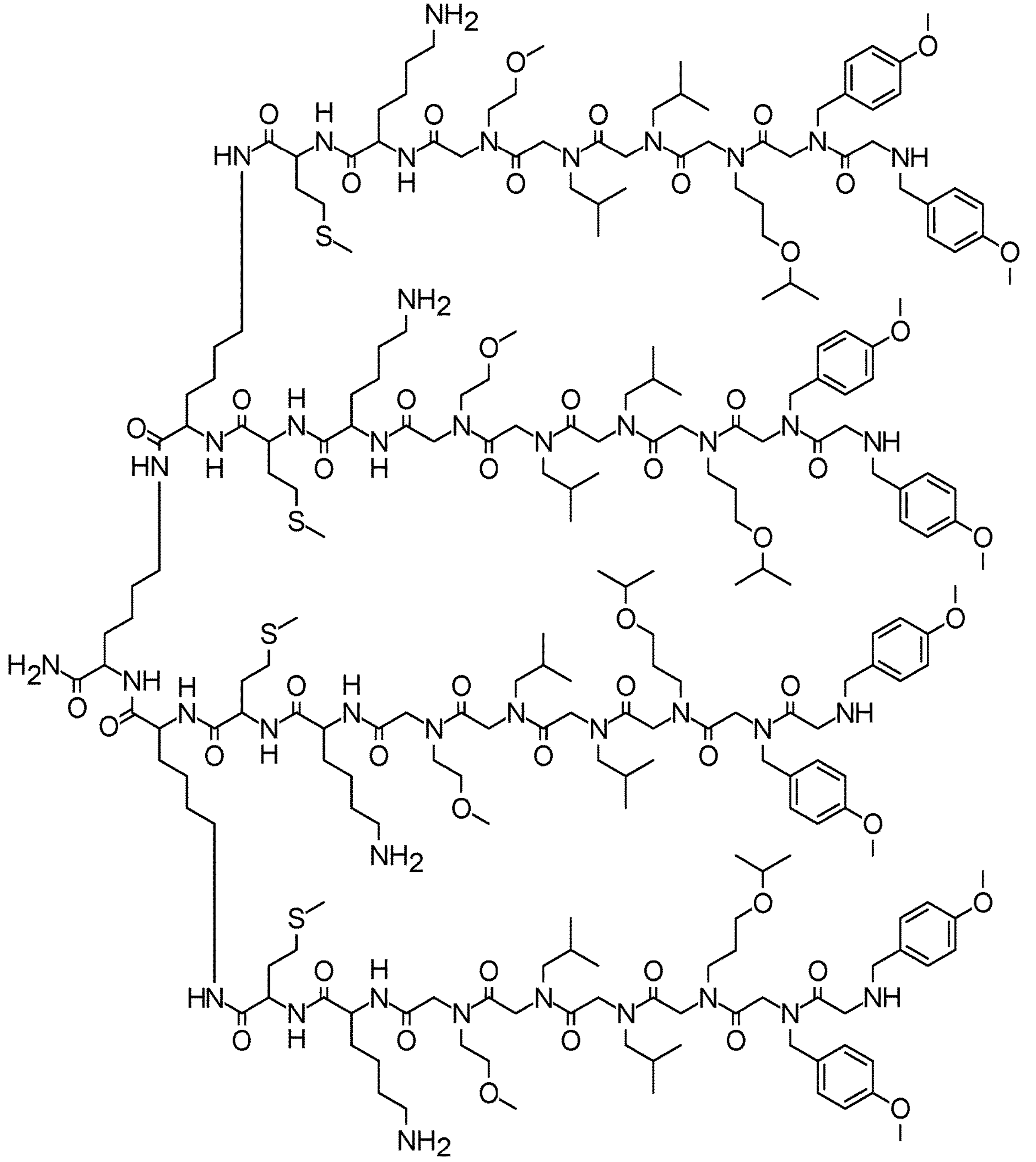

Example 1.4. Confirmation of ACE2P1 and ACE2P2 Binding to Human $ACE2^+$ Cells Applicant resynthesized the identified ACE2P1 and ACE2P2 peptoids on-bead and introduced human $ACE2^+$ (red stained) and $ACE2^-$ (green stained) MCF-7 cells separately to these two peptoid carrying beads. As shown in FIG. 6, the beads bound only to red stained $ACE2^+$ cells and not to green stained $ACE2^-$ cells.

Example 1.5. Optimization of ACE2P1 and ACE2P2

Because Applicant's previous peptoid multimerizations improved cell surface receptor binding dramatically, Applicant immediately developed dimeric, trimeric and tetrameric (quaternary) versions of ACE2P1 and ACE2P2. The multimeric structures are shown in FIGS. 7A-F. These multimers include ACE2P1D1, ACE2P2D1, ACE2P1T1, ACE2P2T1, ACE2P1Q1, ACE2P2Q1.

Example 1.6. Confirmation of Direct Binding of ACE2P1 and ACE2P2 to ACE2

Figure 8A:
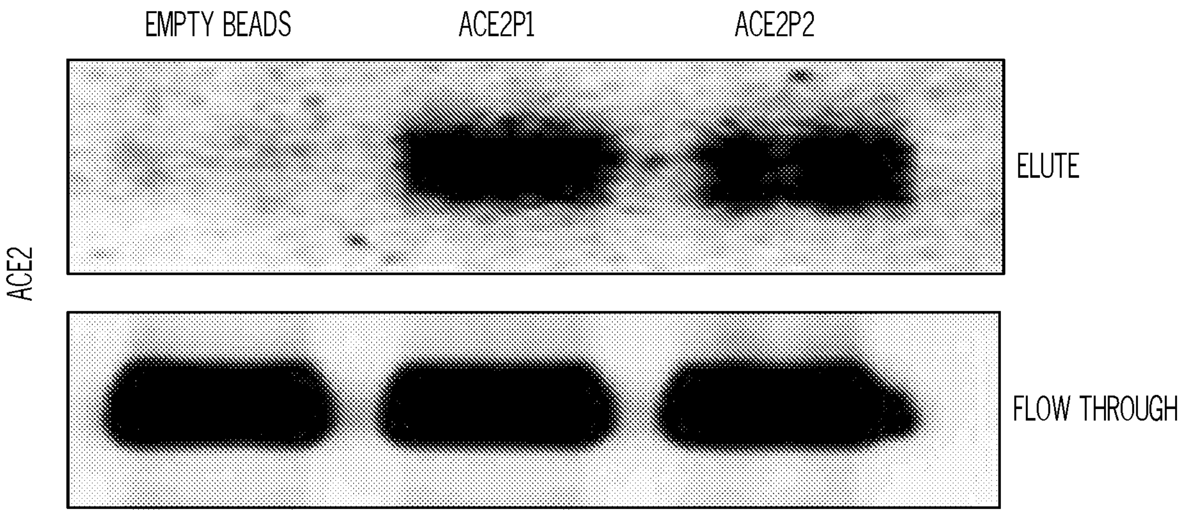
FIGS. 8A-D illustrate that ACE2P1 and ACE2P2 interact directly with ACE2.

To confirm a direct interaction between the peptoids and ACE2, Applicant performed in vitro pulldown assays. Recombinant human ACE2 protein was incubated with ACE2P1 or ACE2P2 conjugated beads at 4° C. overnight. The beads were then washed with PBS buffer for 3 times, and the binding proteins were eluted with 1% SDS. The yielded lysates were then applied onto 10% SDS-PAGE gel and subjected to western blotting (FIG. 8A). Both ACE2P1 and ACE2P2 were able to pull down the ACE2 protein.

Figure 8B:
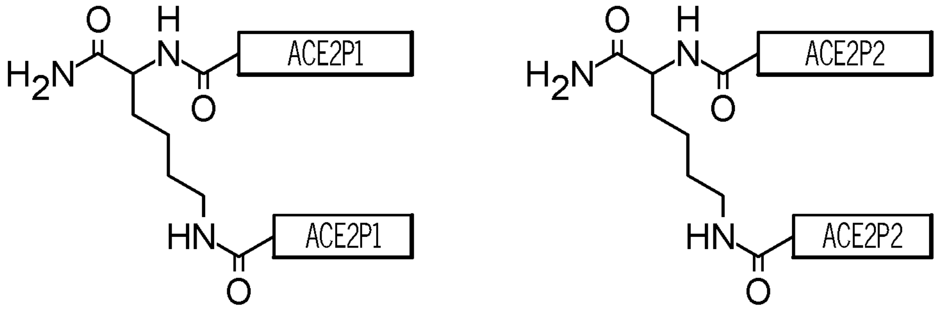

Next, Applicant created the dimers of ACE2P1 and ACE2P2 (FIG. 8B) and performed thermal shift assays using recombinant ACE2 proteins. Thermal shift assay is routinely used in drug discovery to identify protein-ligand interactions. The Applied Biosystems™ Protein Thermal Shift™ assay measures protein thermal stability using a fluorescent protein-binding dye. The Protein Thermal Shift dye does not fluoresce in aqueous solutions but fluoresces in nonpolar environments. The protein is mixed with the dye and heated. As it unfolds or melts, hydrophobic parts of the protein are exposed and bind to the dye, resulting in fluorescence emission detected by the qPCR system. Binding of a ligand to the protein changes the stability of the protein, resulting in a change in fluorescence intensity.

Figure 8C:
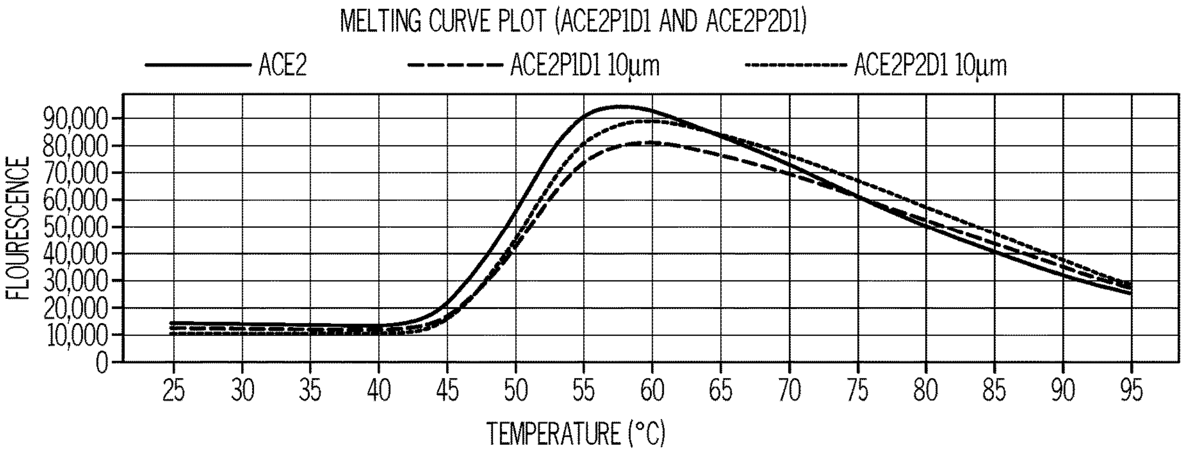
Figure 8D:
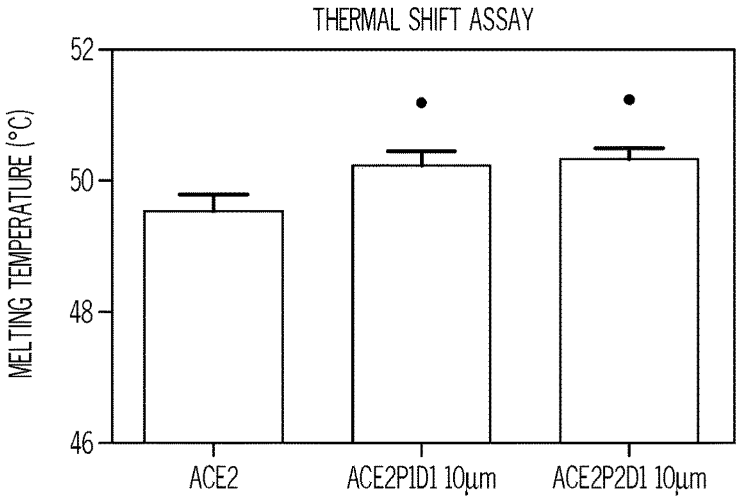

As shown in FIGS. 8C and 8D, when recombinant ACE2 is mixed with ACE2P1D1 or ACE2P2D1, an increase in protein melting temperature was observed. The aforementioned results indicate a direct interaction between these compounds and ACE2.

Example 1.7. Quantification of Peptoids Binding to ACE2

Figure 9:
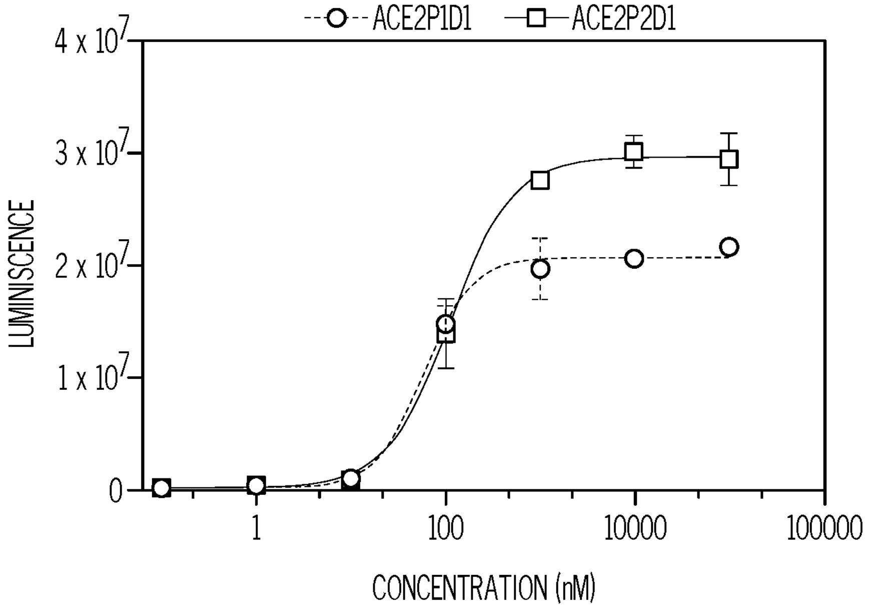
FIG. 9 illustrates that ACE2P1D1 and ACE2P2D1 interact with ACE2 at a low nano-molar binding affinity. Shown are the results of an ELISA-like quantitative binding assay of ACE2P1D1 and ACE2P2D1 binding to ACE2 recombinant protein. The luminescence was measured as an indicator of bound peptoids to increasing concentrations to ACE2. ACE2P1D1 and ACE2P2D1 bind to ACE2 at $K_d$ values of 60 nM and 110 nM, respectively.
Figure 10A:
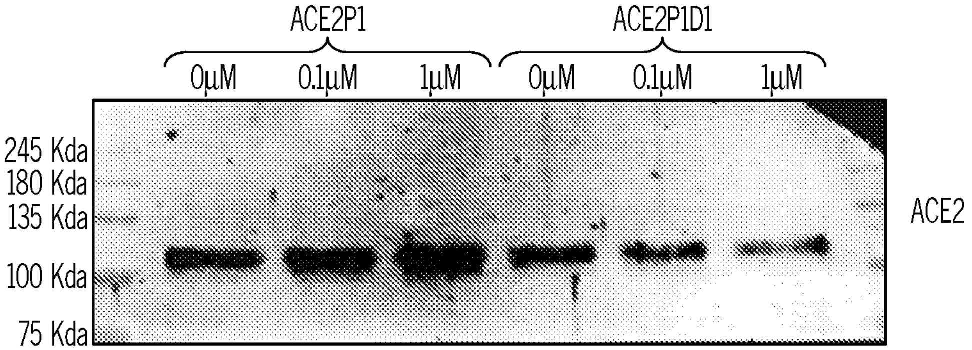
FIGS. 10A-D illustrate that ACE2P1D1 and ACE2P2D1 prevented the binding of spike protein to ACE2. Pure recombinant ACE2 protein and pure recombinant GST-tagged SARS-CoV-2 spike proteins were mixed together. Interaction between the two proteins was then assessed by GST pull-down assay. ACE2P1 (FIGS. 10A-B) and ACE2P2 (FIG. 10C) dimers were premixed with ACE2 for 30 minutes before the mixture was applied to the GST pull-down assay to determine if these compounds can block the interaction between ACE2 and spike protein.
Figure 10B:
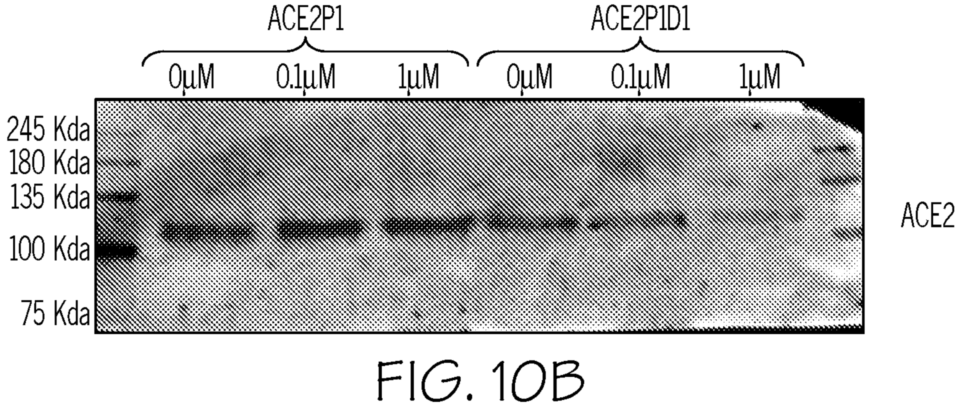
Figure 10C:
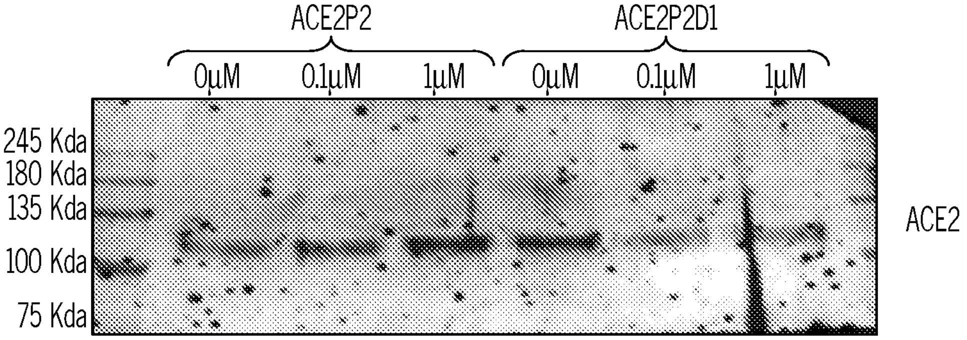
Figure 10D:
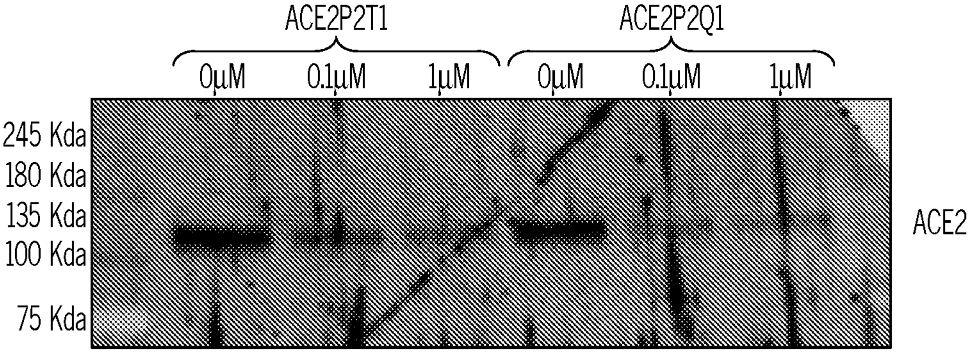

In order to quantify the binding event of ACE2P1D1 and ACE2P2D1 to ACE2, Applicant performed ELISA-like quantitative binding assay using the commercially available ACE2 recombinant protein. The ACE2 protein with his-tag was coated onto 96-well Ni-coated plates and biotinylated peptoids were introduced with increasing concentrations. The bound peptoids were probed with the streptavidin-HRP system by measuring the enzymatic activity through luminescence on Spectramax spectrophotometer. The data was plotted as shown in FIG. 9. As also shown in FIG. 9, the dissociation constants ($K_d$ binding) were found to be 60 nM and 110 nM for ACE2P1D1 and ACE2P2D1, respectively.

Example 1.8. ACE2P1 and ACE2P2 Block SARS-CoV-2 Spike Protein Binding to Human ACE Applicant used GST pull-down assays to determine whether ACE2P1 and ACE2P2 can block the interaction between spike protein and ACE2. GST pull-down assay uses affinity capture of the GST-tagged bait protein (in this case, the spike protein). When the GST-tagged bait protein binds to its partner (in this case, ACE2), the resulting complex is captured on beads with immobilized glutathione and pulled down from the solution.

The Pierce GST Tag Protein Interaction Pull-Down Kit was used in this assay. Applicant pulled down the protein complex with glutathione agarose to catch GST, then detect ACE2 by western blot. As shown in FIG. 10, dimers of ACE2P1 and all 3 forms of multimers (dimers, trimers and tetramers) of ACE2P2 can prevent the binding of spike protein to ACE2.

As also shown in FIG. 10, the ACE2P2 series of peptoids blocked spike protein-ACE2 interaction at 1 μM. However, the monomers of both ACE2P1 and ACE2P2 increased the binding of spike protein to ACE2, an interesting opposite effect. Without being bound by theory, it is envisioned that the monomers may change the ACE2 protein conformation in a way that increases binding to spike protein or provide 'sandwich' type interactions to both sides by sitting in the interphase.

Figure 11A:
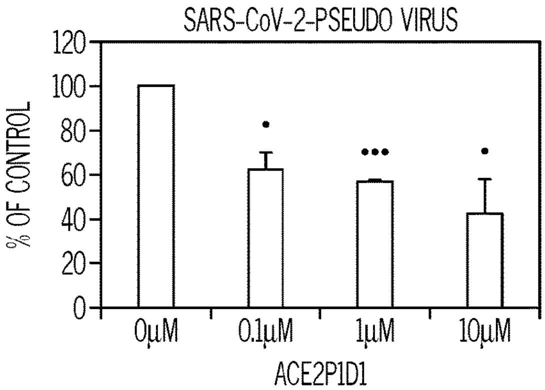
FIGS. 11A-D show that ACE2P1D1 and ACE2P2D1 blocked pseudo virus infection of human cells. H1299 cells were pretreated with ACE2P1D1 (FIG. 11A) or ACE2P2D1 (FIG. 11B) for 1 hour and then infected with SARS-CoV-2 pseudovirus for 24 h. Infection was detected with luciferase reporter assay at 72h. H1299 cells were pretreated with ACE2P1D1 (FIG. 11C) or ACE2P2D1 (FIG. 11D) for 1 hour and then infected with SARS-CoV-2 D614G pseudovirus for 24h. Infection was detected with luciferase reporter assay at 72h.
Figure 11B:
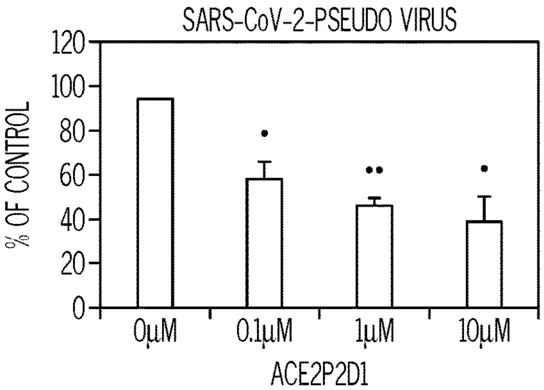

Example 1.9. ACE2P1D1 and ACE2P2D1 Blocked SARS-CoV-2 Pseudo Virus Infection of Human Cells To test the capability of ACE2P1D1 and ACE2P2D1 in blocking SARS-CoV-2 infection, Applicant used a pseudotyped virus to conduct assays in a regular BSL-2 lab. The virus is a lentiviral vector based pseudovirus that contains the luciferase gene for convenient measurement of the virus infectivity. The pseudotyping was done by co-transfecting two lentiviral plasmids (carrying the lentiviral backbone and the rep-cap gene, respectively) with another plasmid that contains the full-length spike gene of SARS-CoV-2. After the titer was determined, the generated pseudovirus was used to infect H1299 human lung cancer cells in the presence or absence of the peptoids. As shown in FIGS. 11A-B, ACE2P1D1 and ACE2P2D1 were effective in inhibiting SARS-CoV-2 pseudovirus infection.

Figure 11C:
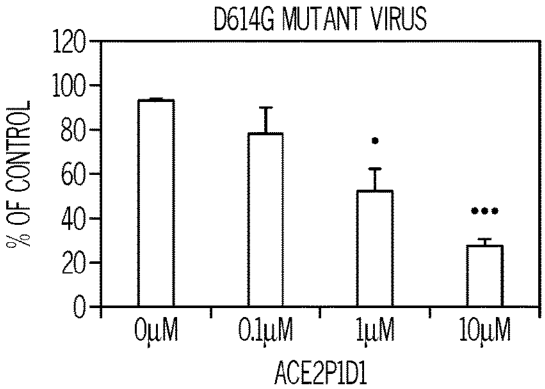
Figure 11D:
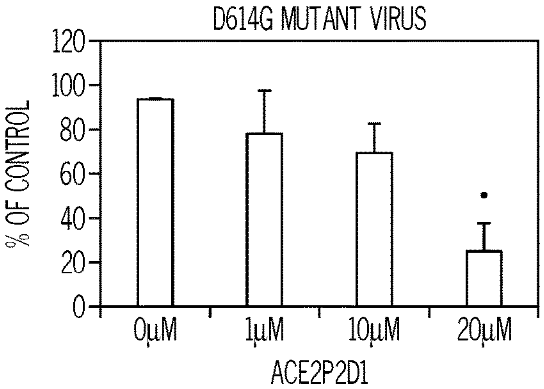

Example 1.10. ACE2P1D1 and ACE2P2D1 Blocked D614G Mutant SARS-CoV-2 Pseudo Virus Infection of Human Cells The D614G mutant pseudovirus was used to infect H1299 human lung cancer cells, in the presence or absence of the peptoids. As shown in FIGS. 11C-D, ACE2P1D1 and ACE2P2D1 were effective in inhibiting SARS-CoV-2 mutant pseudovirus infection.

Example 1.11. ACE2P1D1 and ACE2P2D1 do not Affect the Viability of Human Cells

Figure 12A:
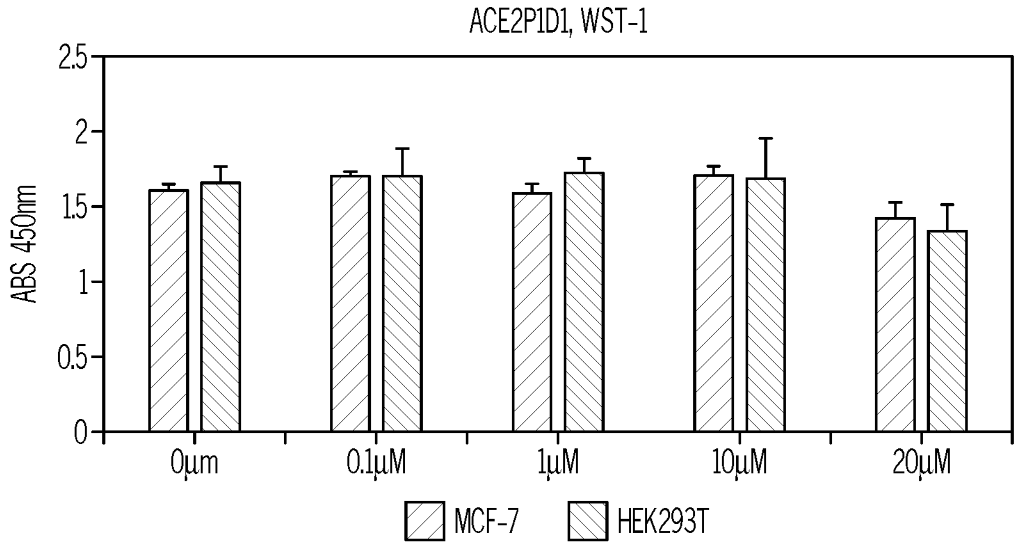
FIGS. 12A-B show that ACE2P1D1 and ACE2P2D1 have no toxicity towards human cells. MCF-7 and HEK293T cells were treated with various concentrations of ACE2P1D1
Figure 12B:
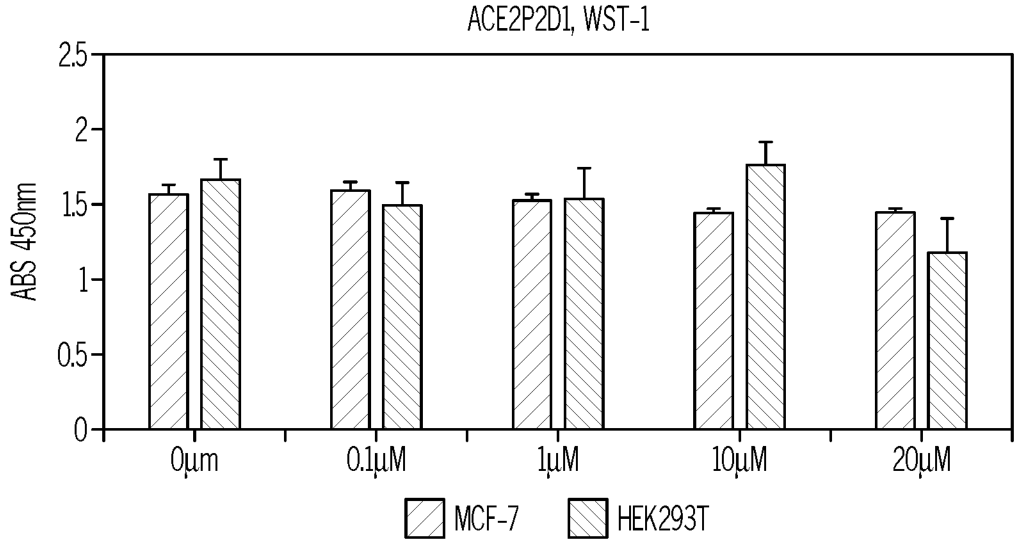
Figure 13A:
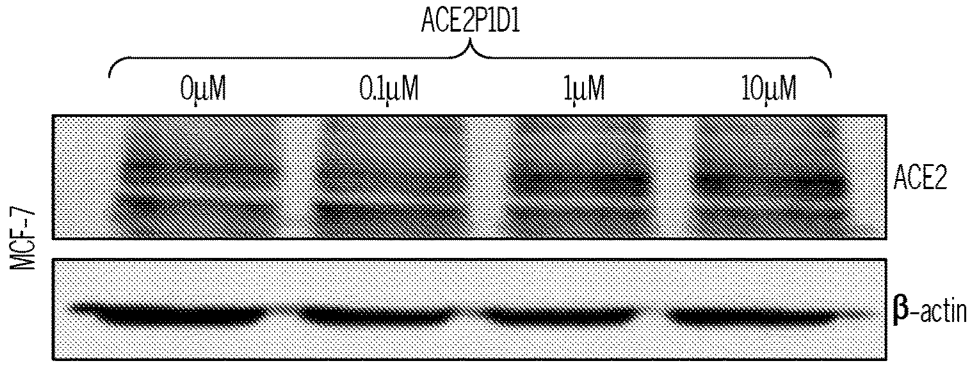
FIGS. 13A-D show that ACE2P1D1 and ACE2P2D1 do not decrease ACE2 expression in human cells. MCF-7 and Caco-2 cells were treated with various concentrations of ACE2P1D1 or ACE2P2D1 for 48 hours. ACE2 expression was determined by western blot analysis.
Figure 13B:
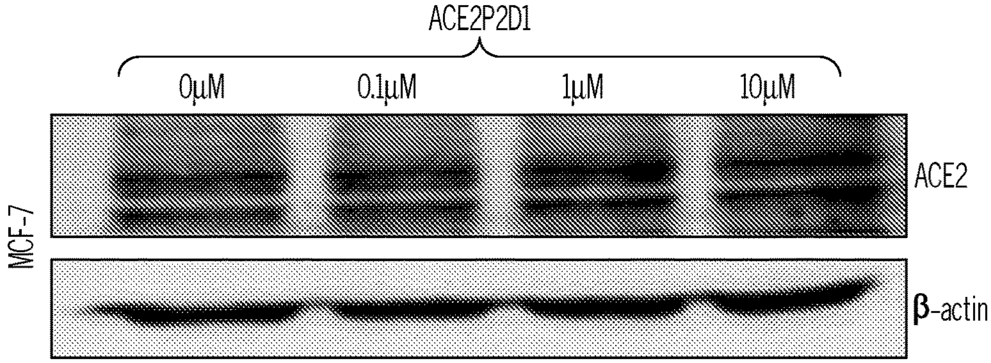
Figure 13C:
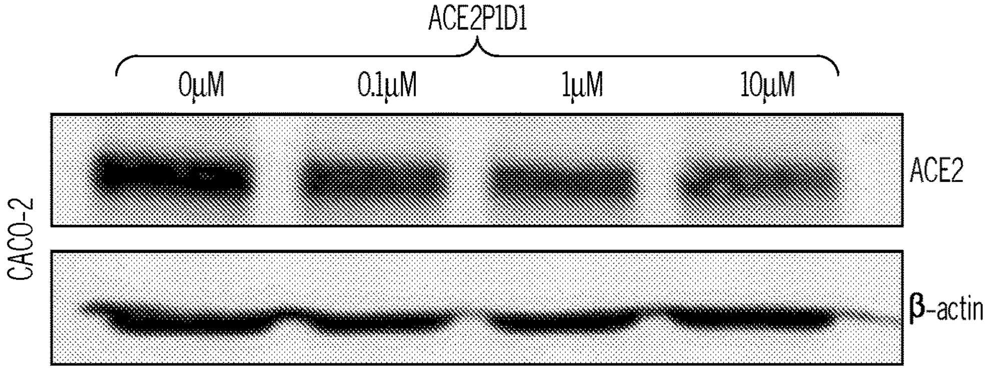
Figure 13D:
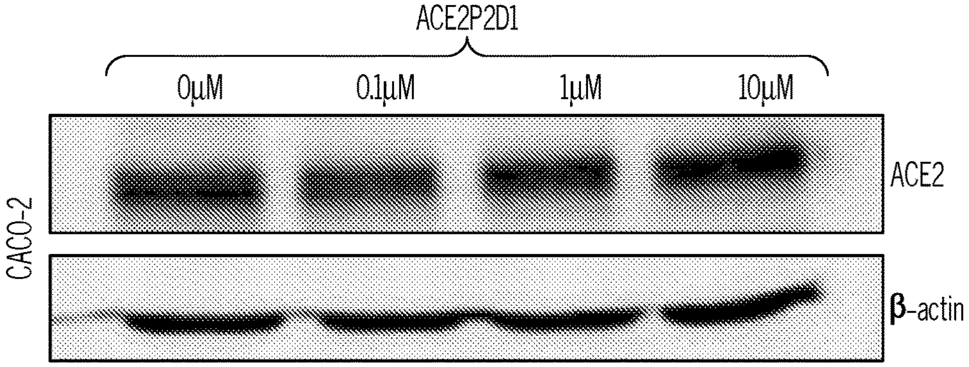

To assess whether the peptoids are toxic to human cells, Applicant performed the WST-1 assay. As shown in FIGS. 12A and 12B, treatments with various concentrations of ACE2P1D1 and ACE2P2D1 had no effects on the viability of human MCF-7 and HEK293T cells.

Example 1.12. ACE2P1D1 and ACE2P2D1 do not Decrease ACE2 Expression in Human Cells As ACE2 is important in blood pressure regulation, Applicant assessed whether the peptoids can decrease ACE2 expression in human cells. As shown in FIGS. 13A-D, treatments with various doses of ACE2P1D1 and ACE2P2D1 did not decrease the expression levels of ACE2 protein.

Example 1.13. ACE2P1D1 and ACE2P2D1 do not Affect the Enzymatic Activity of Human ACE2

Figure 14A:
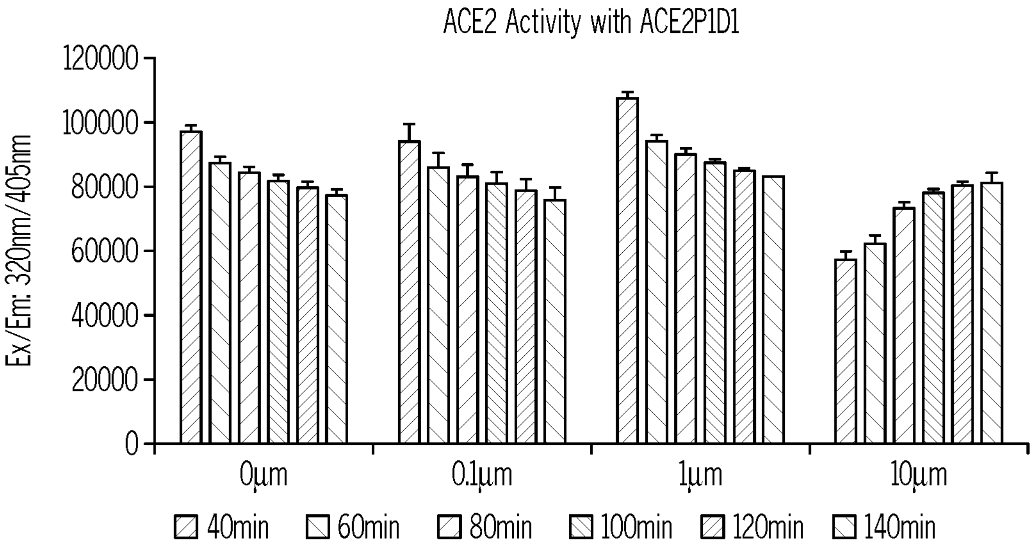
FIGS. 14A-B show that ACE2P1D1 and ACE2P2D1 do not affect the enzymatic activity of ACE2. Assays were run at 37° C. in an ACE2 reaction buffer containing 10 μM Mca-YVADAPK(Dnp), in a total volume of 100 μl. Fluorescence emission at 405 nm, after excitation at 320 nm, was measured in a microplate reader. Cleavage of the substrate Mca-YVADAPK (Dnp) by ACE2 enzyme produces fluorescence. The strength of the fluorescence indicates the ACE2 enzymatic activity.
Figure 14B:
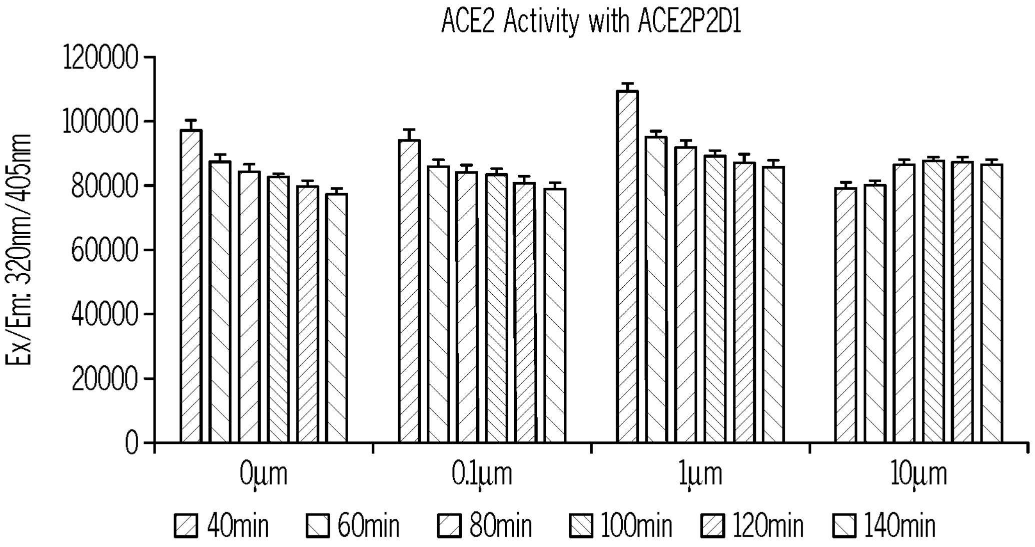

ACE2 is an enzyme that lowers blood pressure by catalyzing the hydrolysis of angiotensin II. Since ACE2's enzyme activity is beneficial to blood pressure regulation, it is important that the peptoids in this Example do not inhibit ACE2. Applicant assessed the effects of ACE2P1D1 and ACE2P2D1 on ACE2 enzyme activity on recombinant ACE2 protein. As shown in FIGS. 14A-B, up to 10 μM of the peptoids have no effects on ACE2 activity.

Figure 15A:
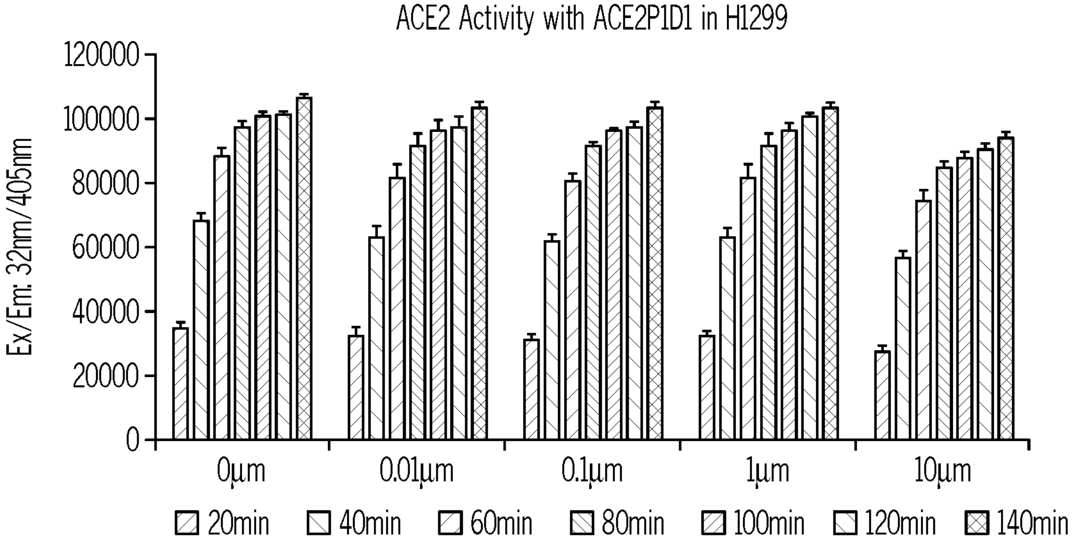
FIGS. 15A-B show that ACE2P1D1 and ACE2P2D1 do not affect the enzymatic activity of ACE2 in human H1299 cells. Assays were run at 37° C. in an ACE2 reaction buffer containing 10 μM Mca-YVADAPK (Dnp), in a total volume of 100 μl. Fluorescence emission at 405 nm, after excitation at 320 nm, was measured in a microplate reader. Cleavage of the substrate Mca-YVADAPK (Dnp) by ACE2 enzyme produces fluorescence. The strength of the fluorescence indicates the ACE2 enzymatic activity.
Figure 15B:
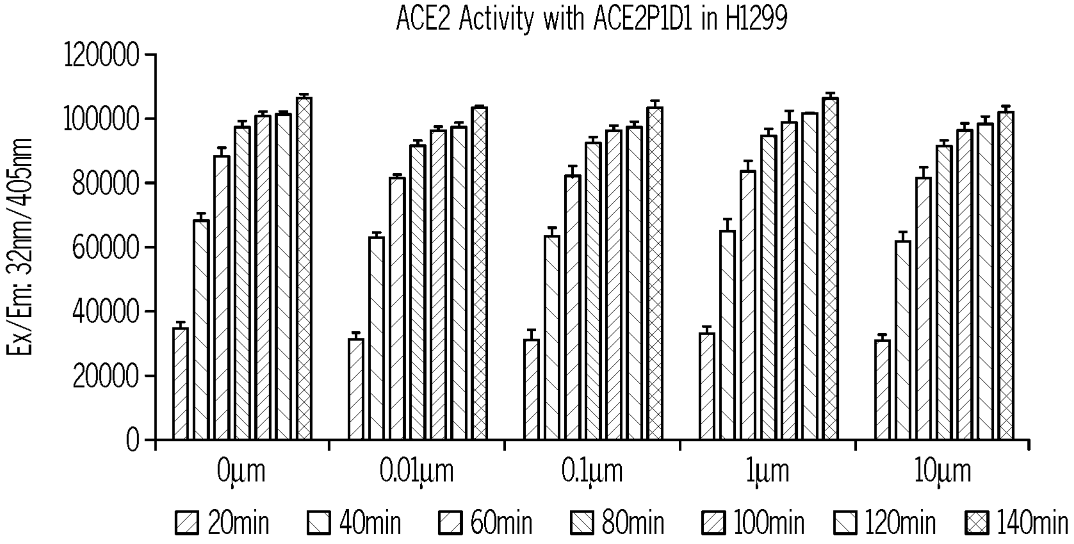
Figure 16A:
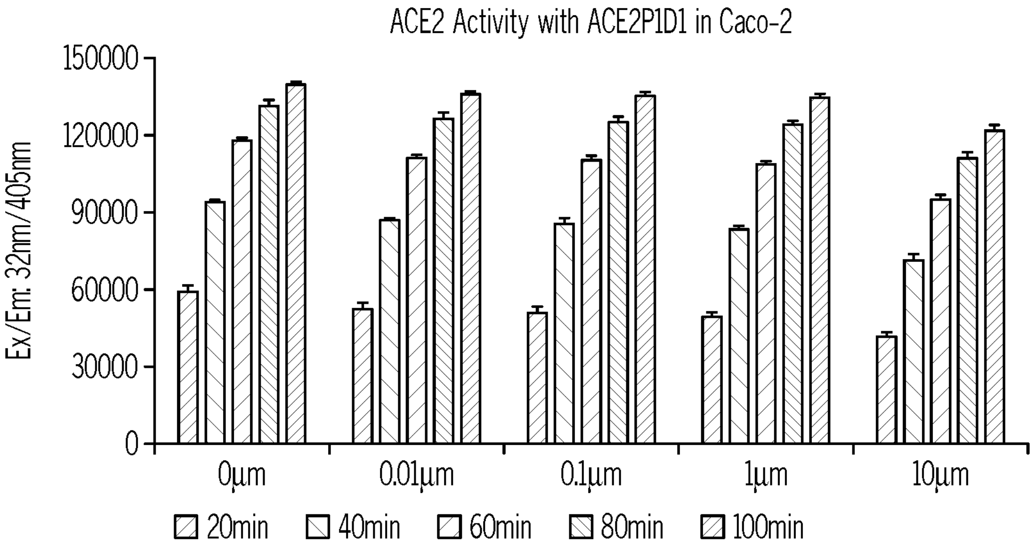
FIGS. 16A-B show that ACE2P1D1 and ACE2P2D1 do not affect the enzymatic activity of ACE2 in human Caco-2 cells. Assays were run at 37° C. in ACE2 reaction buffer containing 10 μM Mca-YVADAPK (Dnp), in a total volume of 100 μl. Fluorescence emission at 405 nm, after excitation at 320 nm, was measured in a microplate reader. Cleavage of the substrate Mca-YVADAPK (Dnp) by ACE2 enzyme produces fluorescence. The strength of the fluorescence indicates the ACE2 enzymatic activity.
Figure 16B:
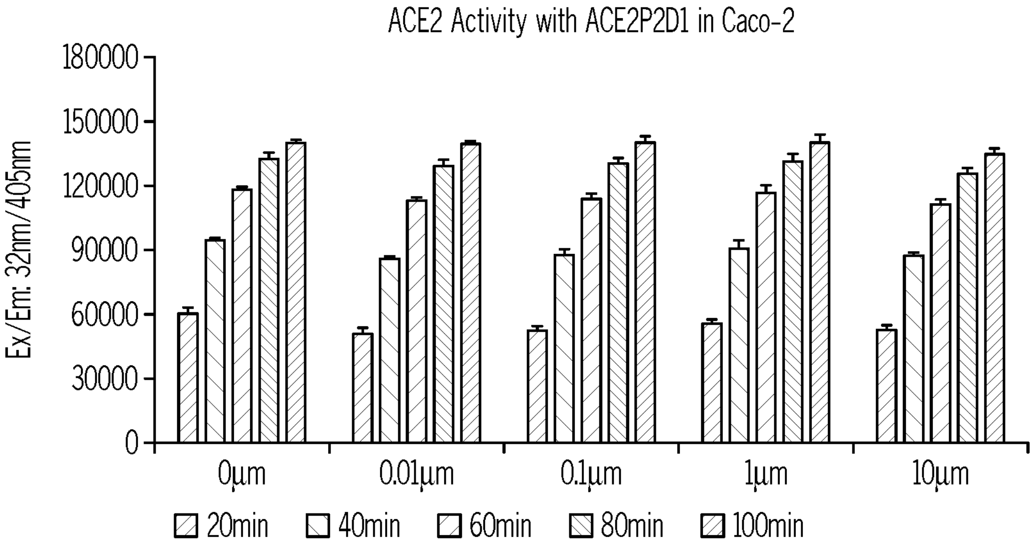
Figure 17A:
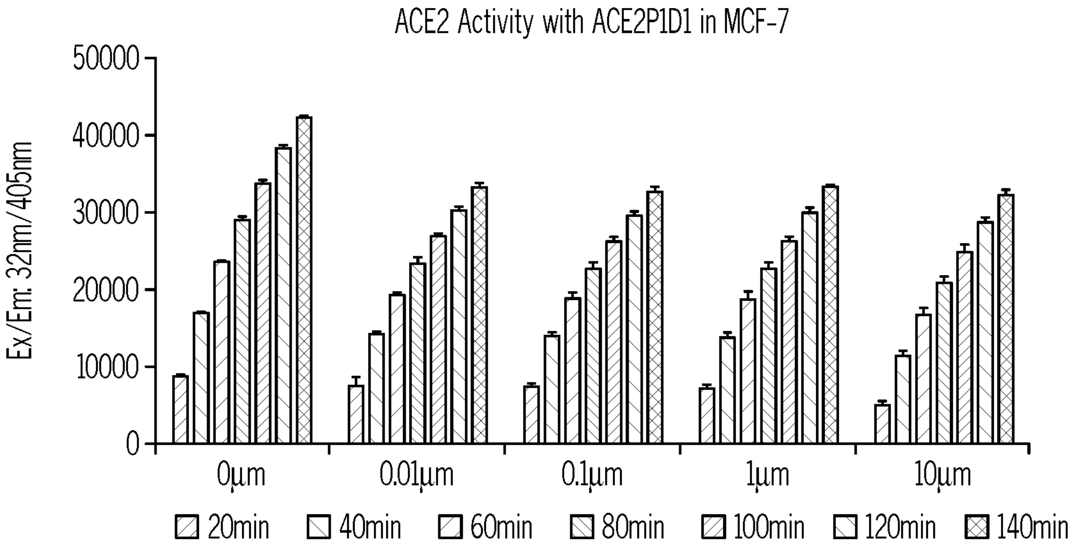
FIGS. 17A-B show that ACE2P1D1 and ACE2P2D1 do not affect the enzymatic activity of ACE2 in MCF-7 cells. Assays were run at 37° C. in an ACE2 reaction buffer containing 10 μM Mca-YVADAPK (Dnp), in a total volume of 100 μl. Fluorescence emission at 405 nm, after excitation at 320 nm, was measured in a microplate reader. Cleavage of the substrate Mca-YVADAPK (Dnp) by ACE2 enzyme produces fluorescence. The strength of the fluorescence indicates the ACE2 enzymatic activity.
Figure 17B:
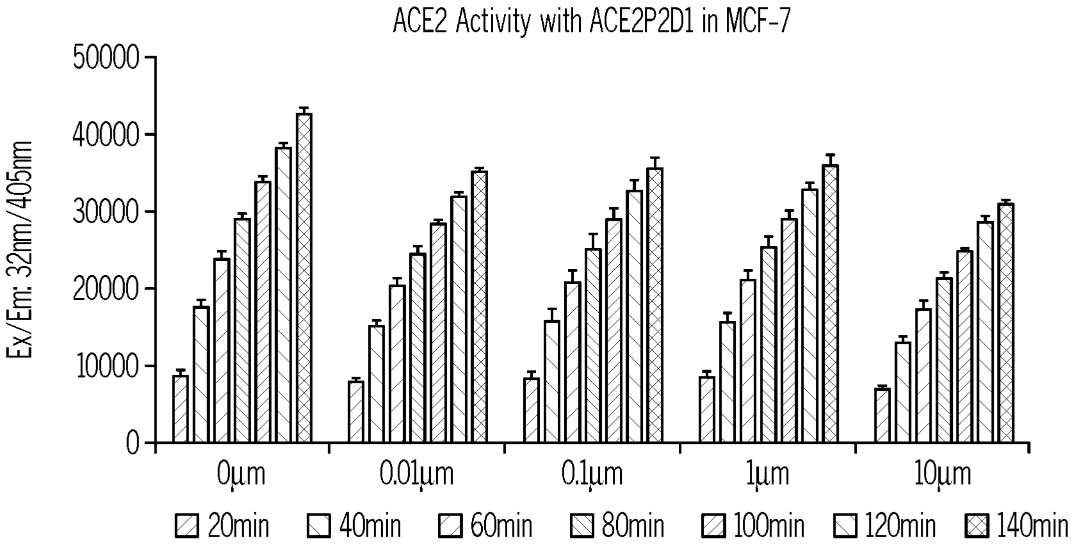

To measure ACE2 activity in cells, cell homogenates were used. To prevent hydrolysis of the substrate by a range of nonmetalloprotease enzymes from the cells, Complete™ Protease Inhibitor Cocktail (Roche/Sigma) were added to the cell homogenates. To eliminate the effects of ACE on the substrate, ACE inhibitor captopril (10 μM) was added to the assay. As shown in FIGS. 15-17, ACE2P1D1 and ACE2P2D1 did not affect the enzymatic activity of ACE2 in human H1299 cells (FIGS. 15A-B), Caco-2 cells (FIGS. 16A-B), and MCF-7 cells (FIGS. 17A-B).

Figure 18A:
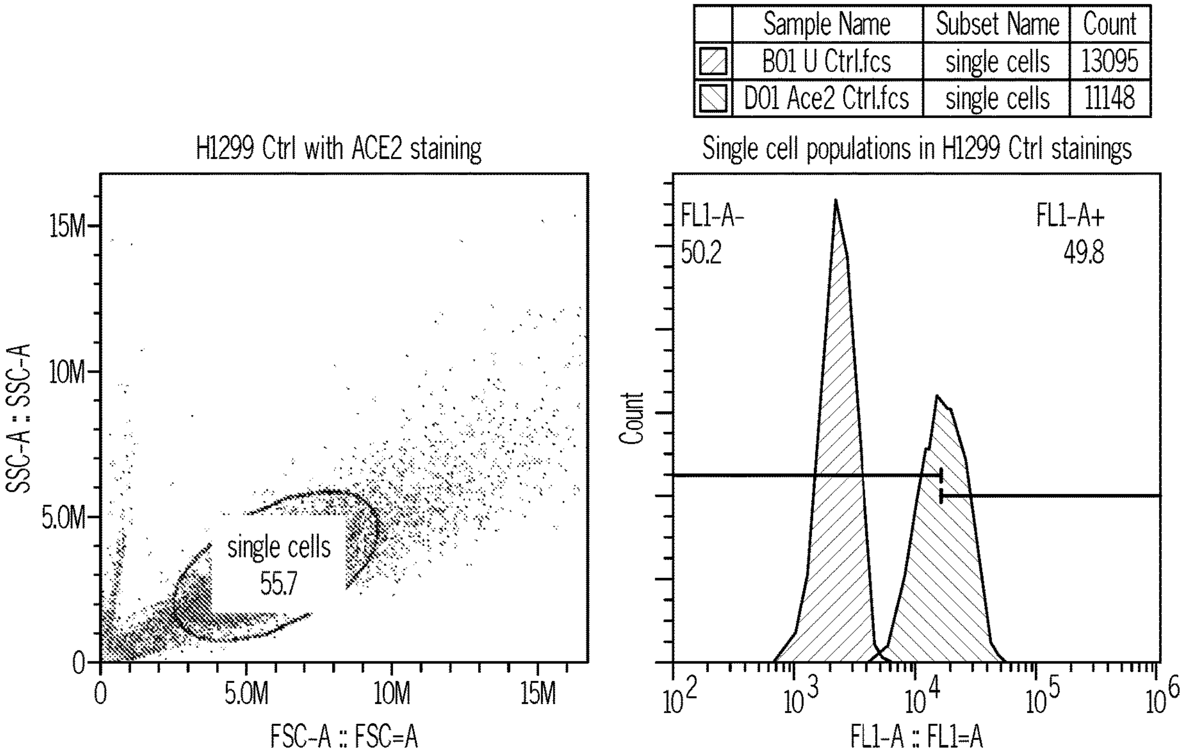
FIGS. 18A-C show that ACE2P1D1 and ACE2P2D1 do not decrease ACE2 expression on cell surfaces. H1299 cells were treated with ACE2P1D1 or ACE2P2D1 for 48 hours. ACE2 surface expression was determined by flow cytometry analysis.
Figure 18B:
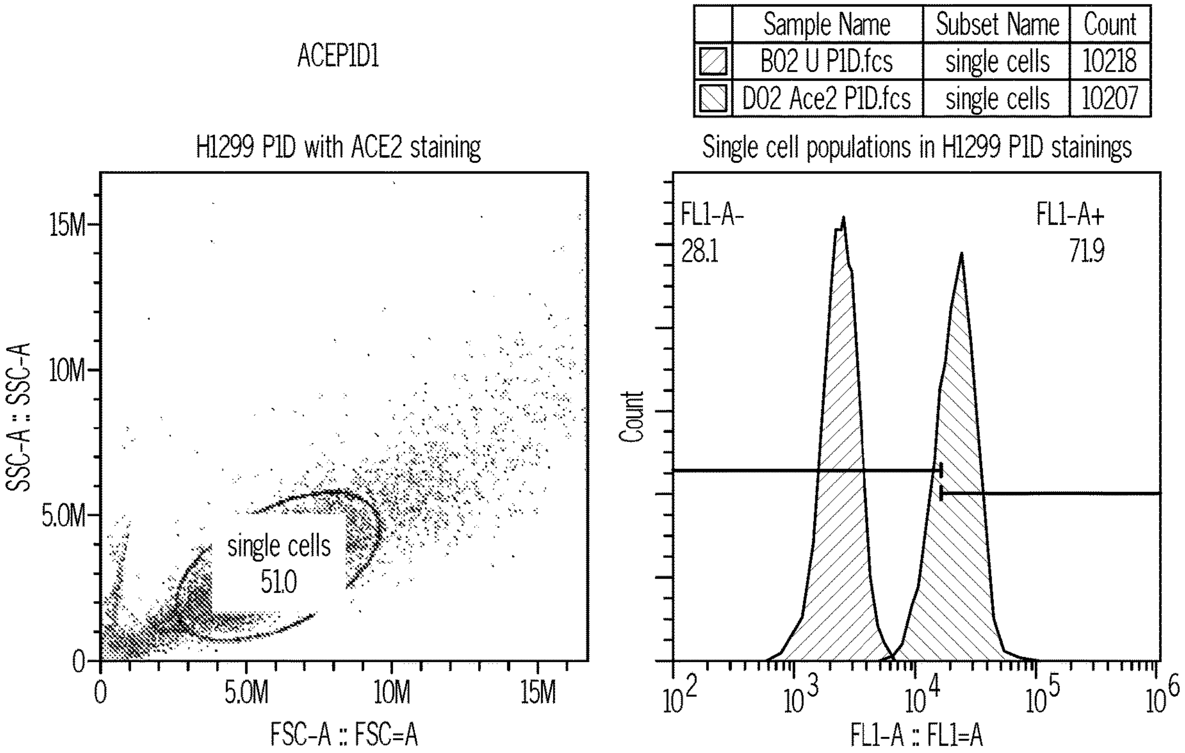
Figure 18C:
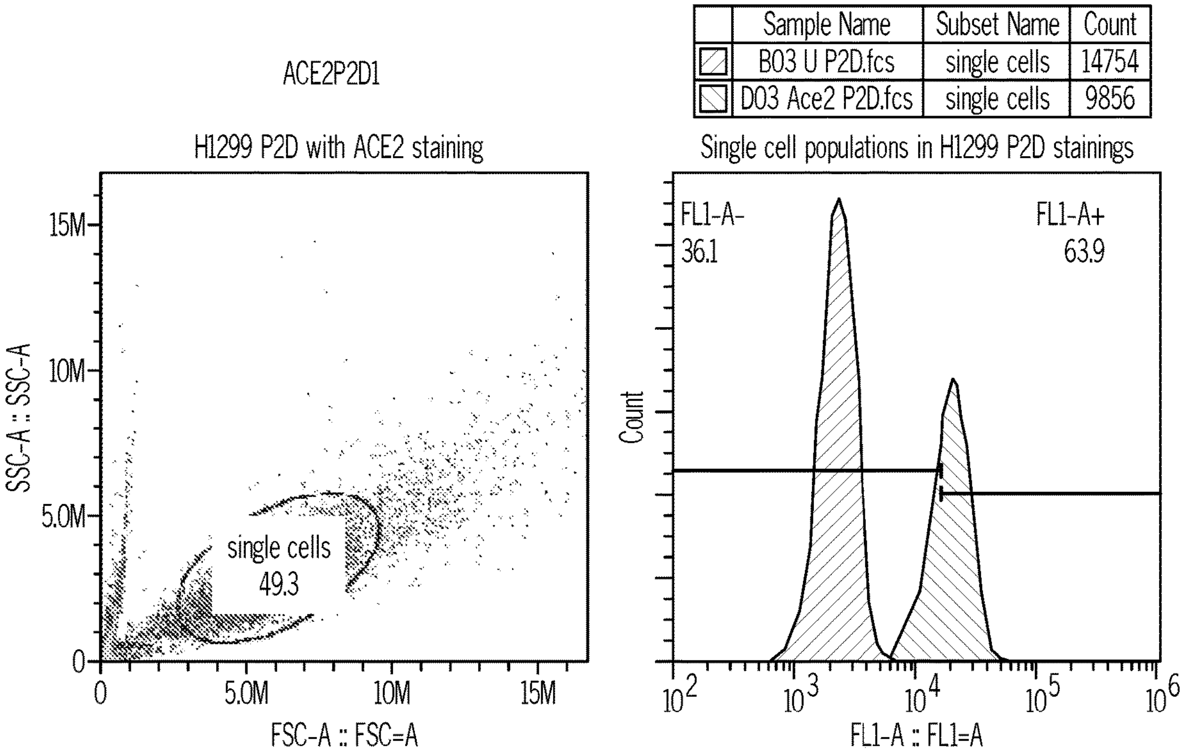

Example 1.14. ACE2P1D1 and ACE2P2D1 do not Decrease ACE2 Expression in Human Cells Next, Applicant determined whether or not the peptoids in this Example can decrease ACE2 levels on a cell surface. Using flow cytometry analysis, Applicant found that treatments with ACE2P1D1 and ACE2P2D1 did not decrease the ACE2 protein levels on cell surface (FIGS. 18A-C).

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of blocking virus entry into cells, said method comprising:

associating the cells with a peptoid, wherein the peptoid is selected from the group consisting of

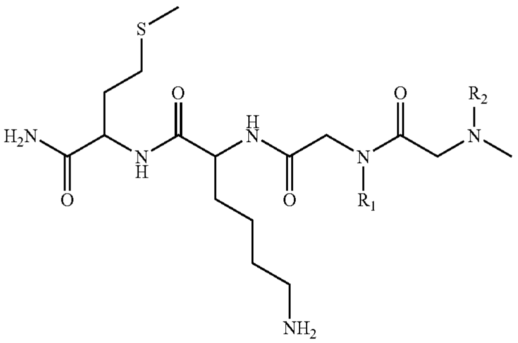

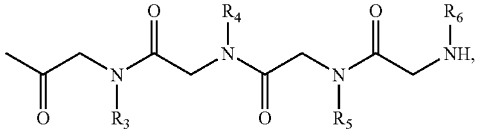

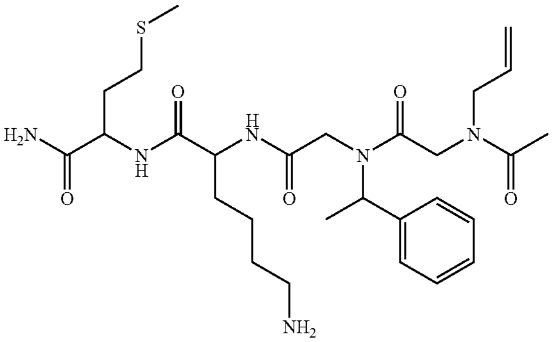

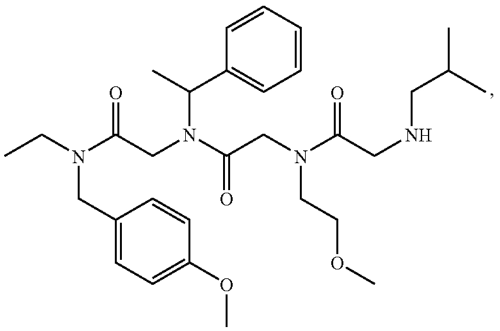

-continued

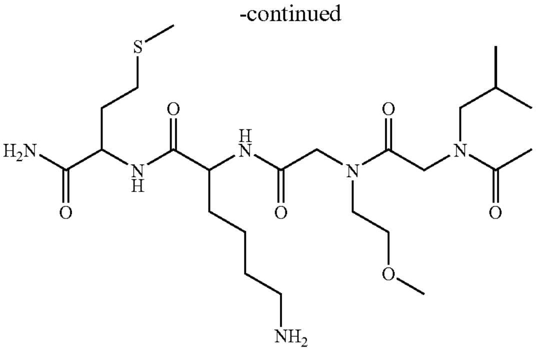

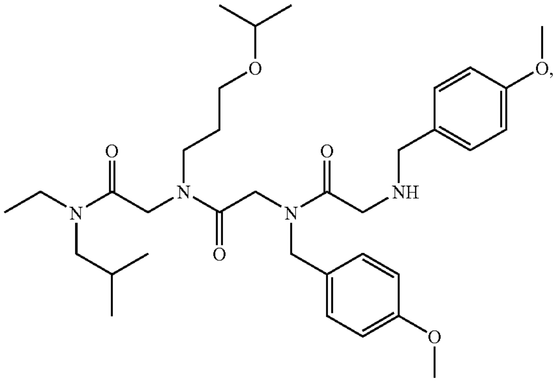

multimers thereof, or combinations thereof, wherein $R_1$, $R_2$, $R_3$, $R_4$, $R_5$, and $R_6$ are each independently selected from the group consisting of

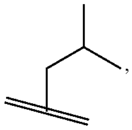
,
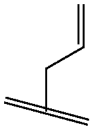
,
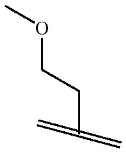
,
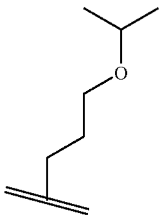
,
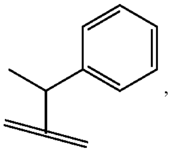
,
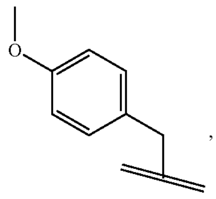
, or combinations thereof, wherein the cells comprise an angiotensin-converting enzyme 2 (ACE2) receptor, and wherein the virus is capable of entering the cells through the ACE2 receptor.

2. The method of claim 1, wherein the peptoid comprises

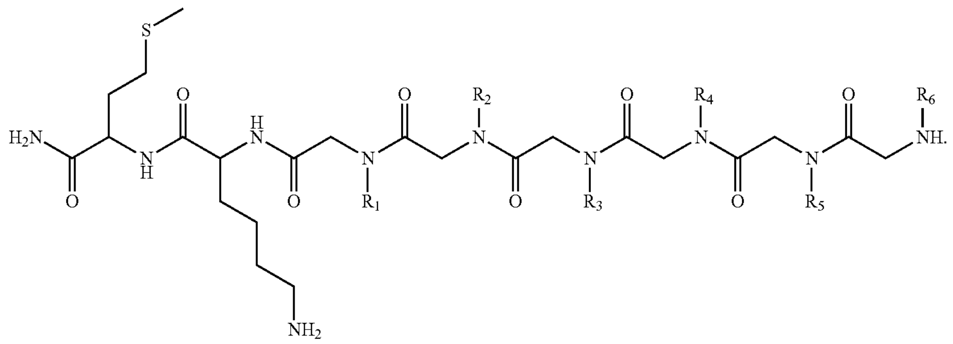

3. The method of claim 1, wherein the peptoid comprises

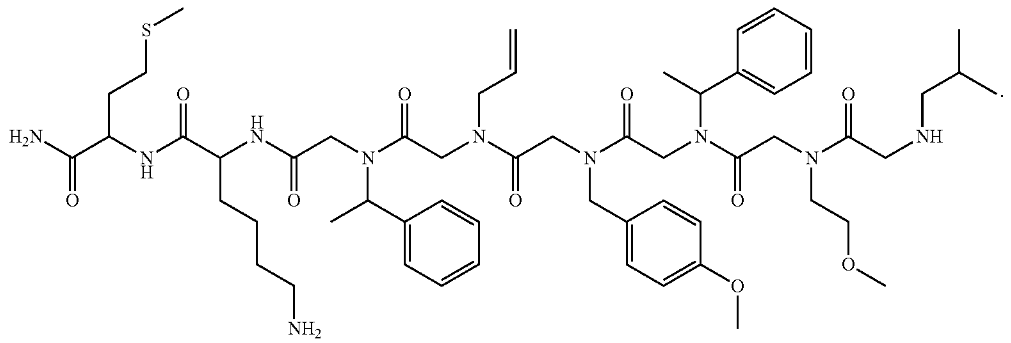 [SMILES: C=CCN(CC(=O)N(CC(=O)NC(CCCCN)C(=O)NC(CCSC)C(N)=O)C(C)c1ccccc1)C(=O)CN(Cc1ccc(OC)cc1)C(=O)CN(C(=O)CN(CCOC)C(=O)CNCC(C)C)C(C)c1ccccc1]

4. The method of claim 1, wherein the peptoid comprises

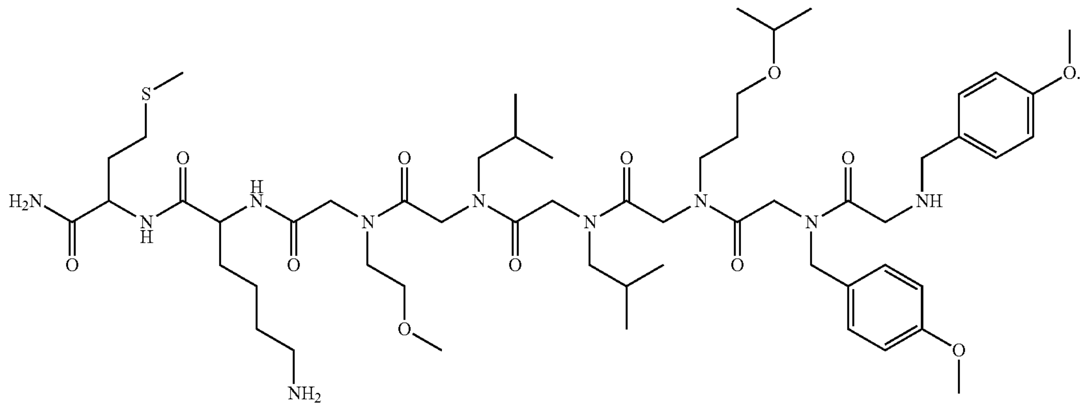 [SMILES: COCCN(CC(=O)NC(CCCCN)C(=O)NC(CCSC)C(N)=O)C(=O)CN(CC(C)C)C(=O)CN(CC(C)C)C(=O)CN(CCCOC(C)C)C(=O)CN(Cc1ccc(OC)cc1)C(=O)CNCc1ccc(OC)cc1]

5. The method of claim 1, wherein the peptoid comprises a multimer, wherein peptoids in the multimer are connected through covalent linkages on peptoid backbones, R groups, at the C-terminus of peptoids, at the N-terminus of peptoids, regions proximal to the N-terminus of peptoids, middle regions of peptoids, regions proximal to the C-terminus of peptoids, or combinations thereof, and wherein the multimer is selected from the group consisting of a homomultimer, a heteromultimer, a cyclic multimer, a dimer, a trimer, a tetramer, or combinations thereof.

6. The method of claim 5, wherein the peptoids in the multimer are connected through one or more linkers, wherein the one or more linkers link peptoids through covalent linkages on peptoid backbones, R groups, or combinations thereof, and wherein the one or more linkers are selected from the group consisting of rigid linkers, semi-rigid linkers, flexible linkers, semi-flexible linkers, cleavable linkers, non-cleavable linkers, lysine-based linkers, glycine-based linkers, cyclic linkers, heterocyclic linkers, alicyclic linkers, non-cyclic linkers, aliphatic linkers, aromatic linkers, sulfide-based linkers, ester-based linkers, ether-based linkers, polyethylene glycol-based linkers, glycol-based linkers, allyl-based linkers, benzyl-based linkers, amino hexanoic-based linkers, NHS ester-based linkers, maleimide-based linkers, and combination thereof.

7. The method of claim 5, wherein the multimer is selected from the group consisting of:
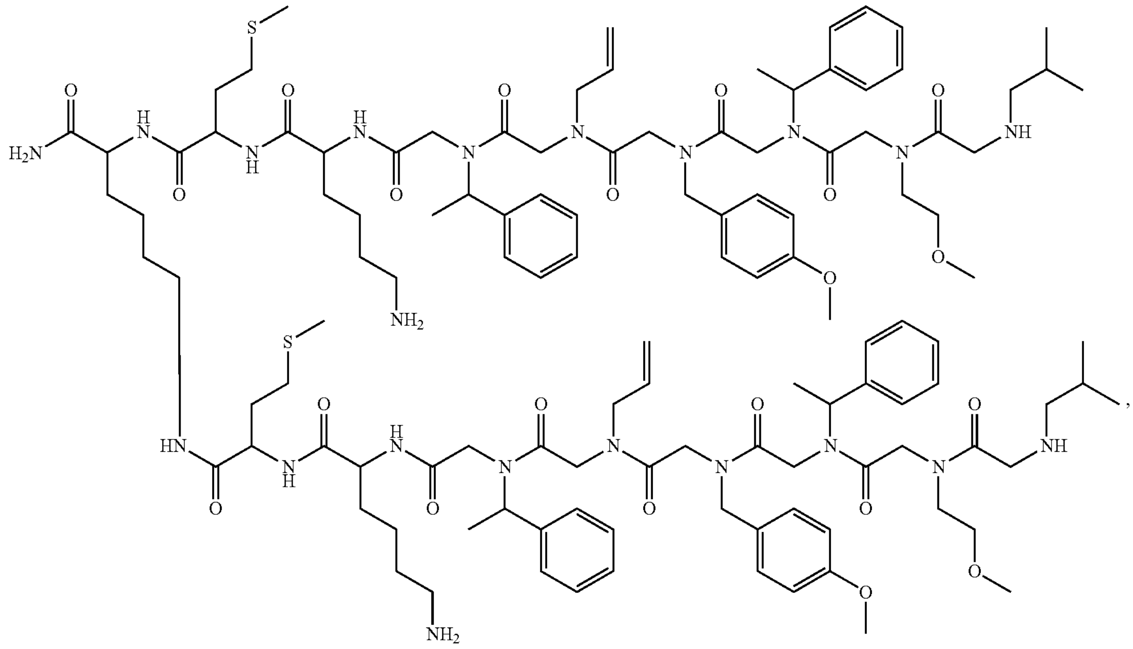
,
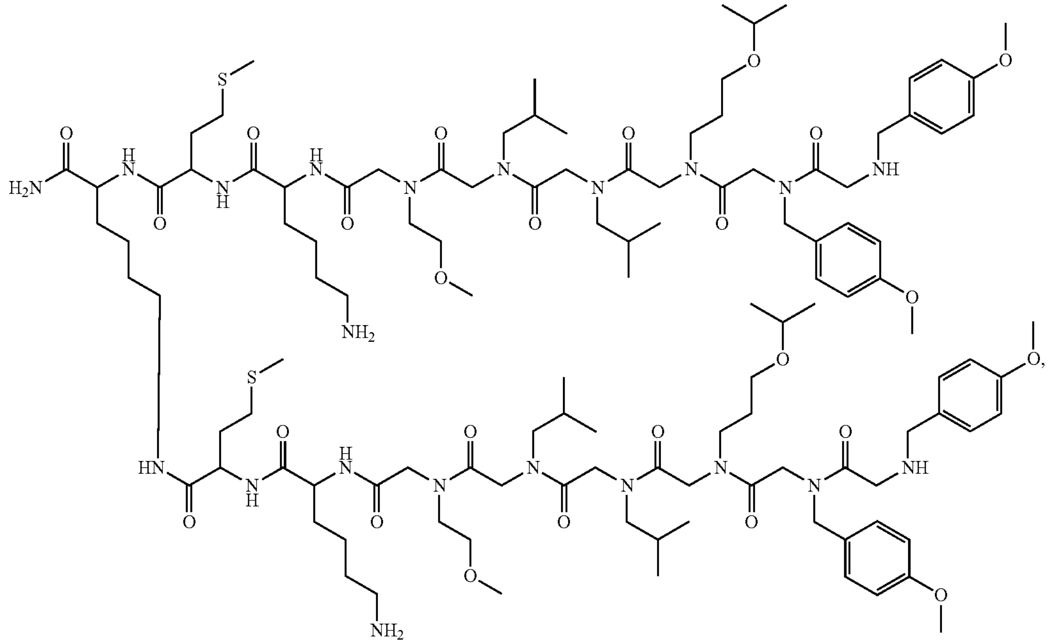
, -continued
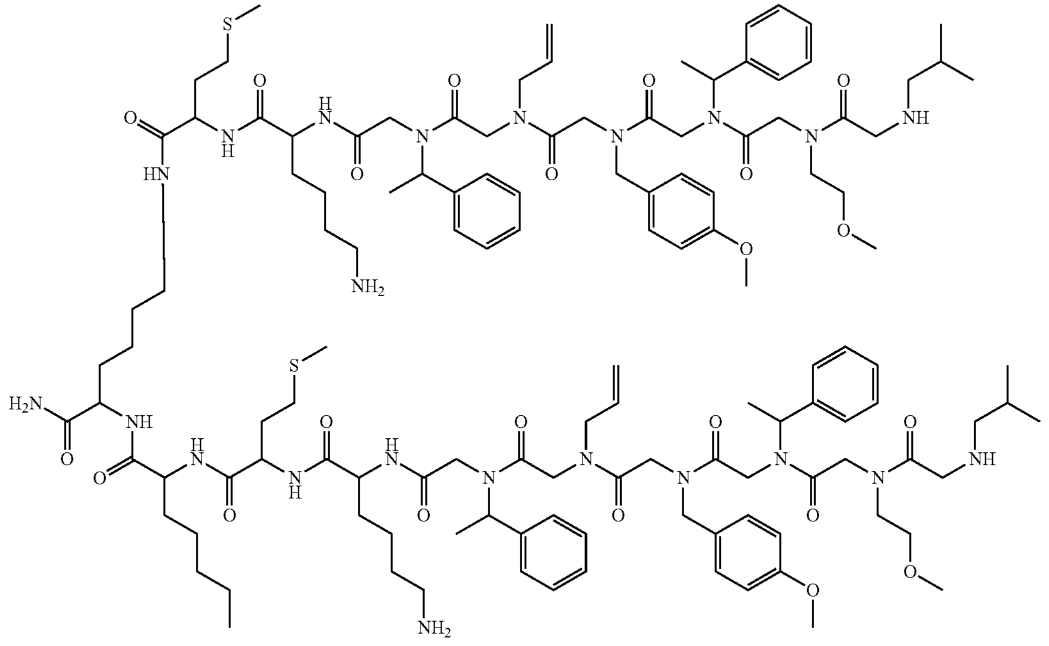
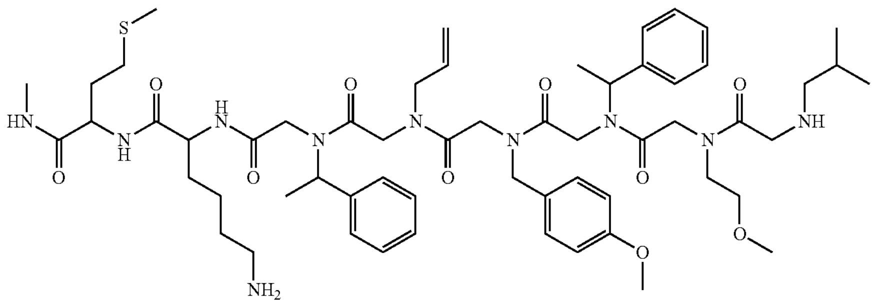
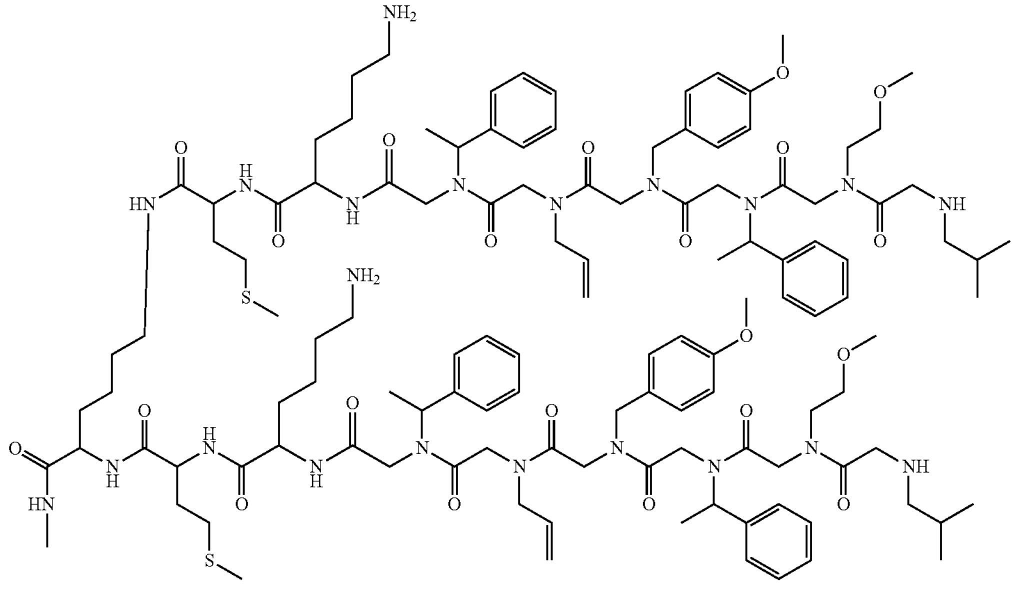

-continued
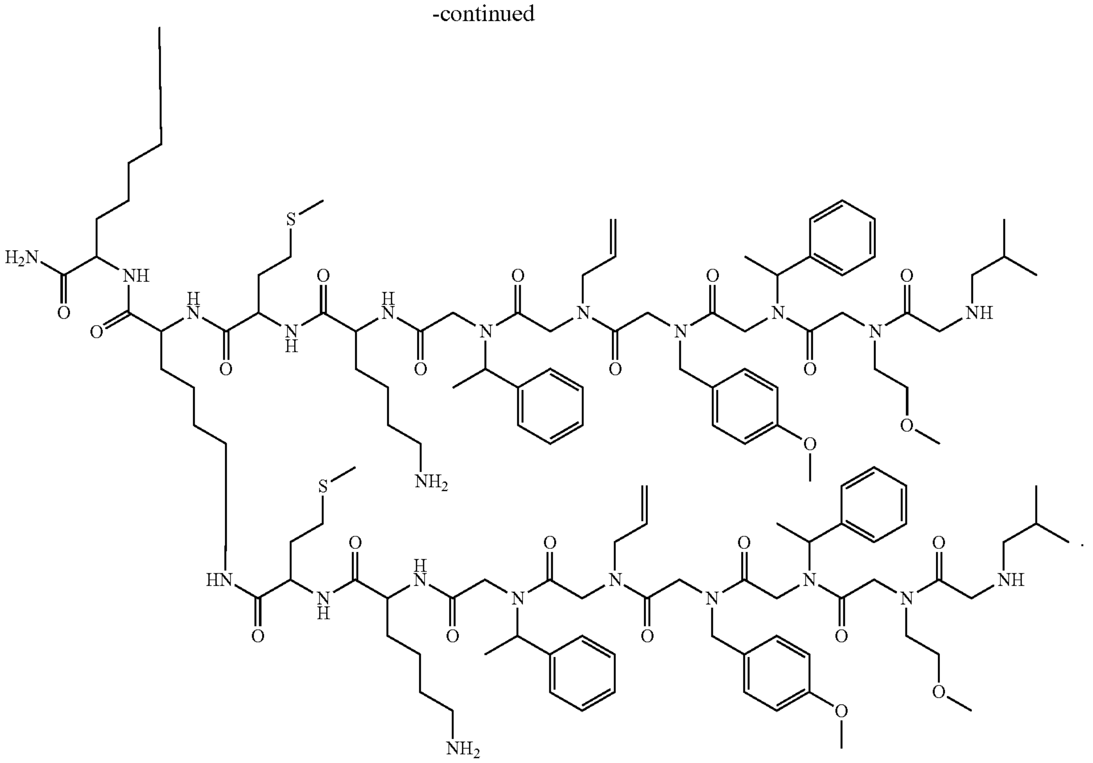
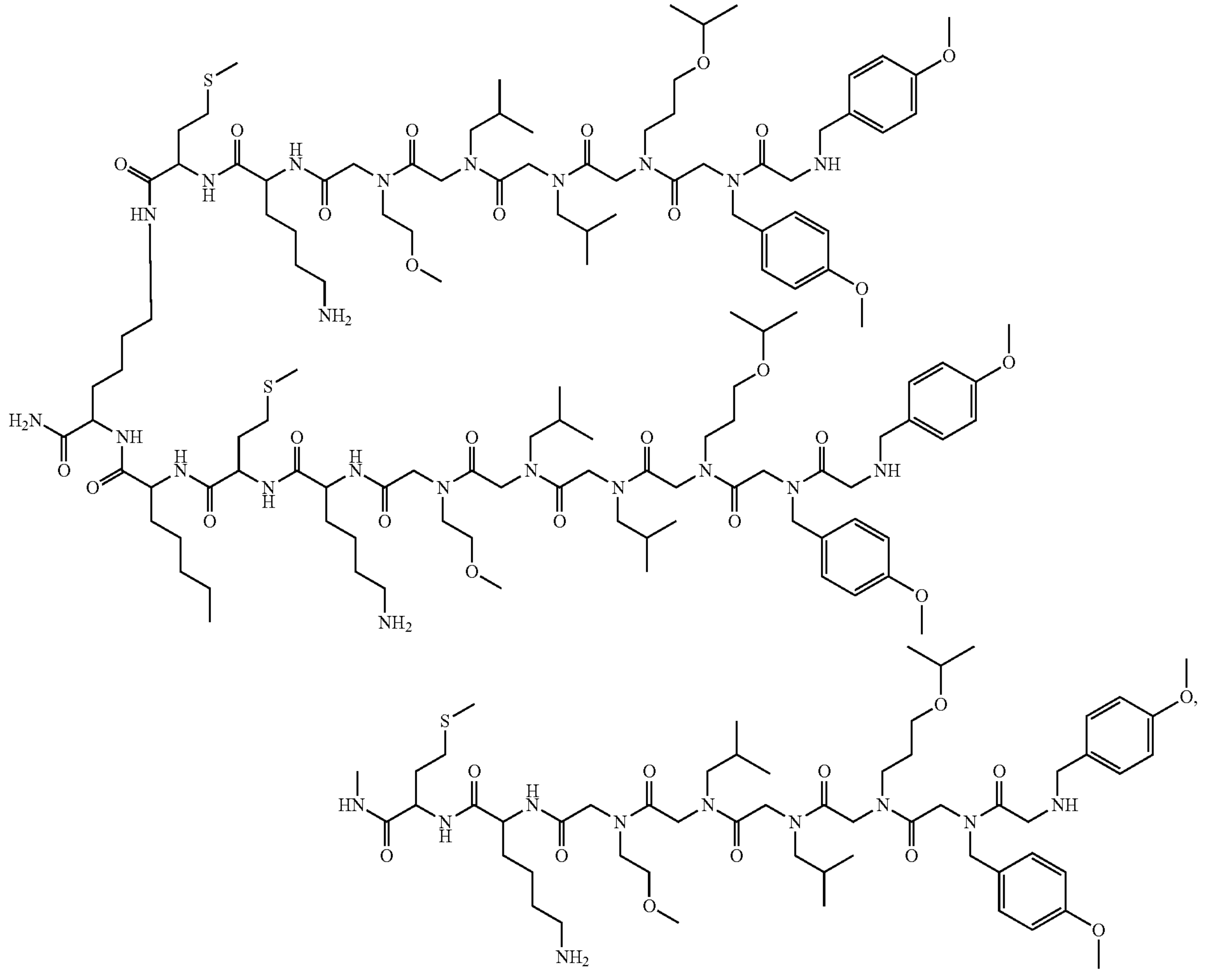

-continued

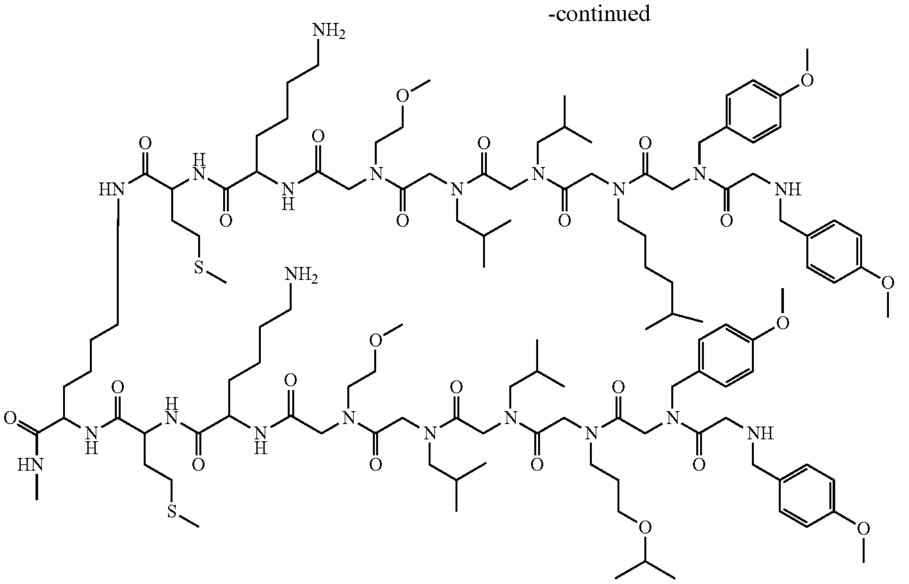

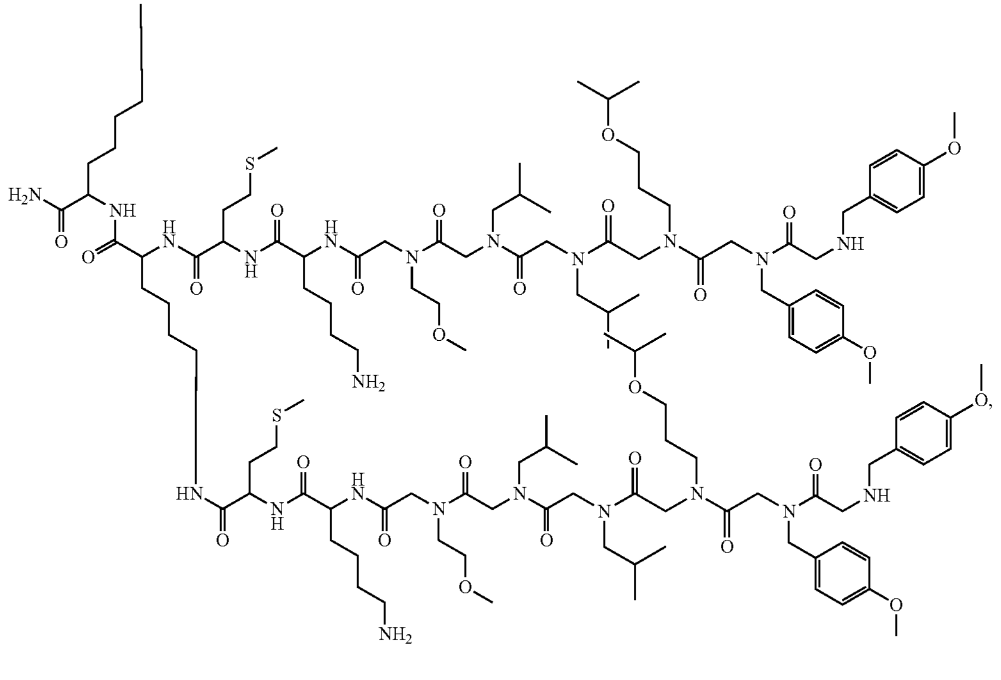

or combinations thereof.

8. The method of claim 1, wherein the peptoid is in a composition, and wherein the composition is in a form selected from the group consisting of nasal sprays, eye drops, injectable suspensions, tablets, or combinations thereof.

9. The method of claim 1, wherein the virus comprises a coronavirus.

10. The method of claim 9, wherein the coronavirus is selected from the group consisting of severe acute respiratory syndrome coronavirus (SARS-CoV), severe acute respiratory syndrome-related coronavirus (SARSr-CoV), human coronavirus 229E (HCoV-229E), human coronavirus NL63 (HCoV-NL63), human coronavirus OC43 (HCoV-OC43), human coronavirus HKU1 (HCoV-HKU1), Middle East respiratory syndrome-related coronavirus (MERS-COV), severe acute respiratory syndrome-related coronavirus 2 (SARS-CoV-2), or combinations thereof.

11. The method of claim 9, wherein the virus comprises severe acute respiratory syndrome-related coronavirus 2 (SARS-CoV-2).

12. The method of claim 1, wherein the cells are selected from the group consisting of endothelial cells, epithelial cells, or combinations thereof.

13. The method of claim 1, wherein the peptoid blocks entry of the virus into cells by binding to ACE 2 receptors on the cells.

14. The method of claim 1, wherein the associating occurs in vitro.

15. The method of claim 1, wherein the associating occurs in vivo in a subject through administration of the composition to the subject.

16. The method of claim 15, wherein the method is utilized to treat or prevent the virus from infecting the subject.

* * * * *